United States Patent
Yamasaki et al.

(10) Patent No.: US 9,102,934 B2
(45) Date of Patent: Aug. 11, 2015

(54) PSEUDO-TISSUE FOR ACCURACY CONTROL, METHOD FOR CONTROLLING ACCURACY BY USING THE SAME, AND METHOD FOR MANUFACTURING THE SAME

(75) Inventors: Masatoshi Yamasaki, Sanda (JP); Yasushi Hasui, Kobe (JP); Chinatsu Fukui, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 682 days.

(21) Appl. No.: 12/057,014

(22) Filed: Mar. 27, 2008

(65) Prior Publication Data
US 2009/0053711 A1    Feb. 26, 2009

(30) Foreign Application Priority Data
Mar. 27, 2007   (JP) ................................ 2007-082147

(51) Int. Cl.
*C12N 15/85* (2006.01)
*C12N 15/10* (2006.01)
(52) U.S. Cl.
CPC .................................. *C12N 15/1003* (2013.01)
(58) Field of Classification Search
None
See application file for complete search history.

(56) References Cited

U.S. PATENT DOCUMENTS

| | | | |
|---|---|---|---|
| 5,853,385 A * | 12/1998 | Emerich et al. | 604/500 |
| 6,251,661 B1 * | 6/2001 | Urabe et al. | 435/287.2 |
| 6,616,912 B2 * | 9/2003 | Eddleman et al. | 424/9.1 |
| 2001/0009991 A1 * | 7/2001 | Hisanaka | 604/364 |
| 2006/0084103 A1 | 4/2006 | Yamasaki et al. | |
| 2007/0027635 A1 | 2/2007 | Yamasaki et al. | |
| 2007/0237749 A1 * | 10/2007 | Wang | 424/93.7 |
| 2008/0206308 A1 * | 8/2008 | Jabbari et al. | 424/426 |
| 2009/0202616 A1 * | 8/2009 | Chong et al. | 424/447 |

FOREIGN PATENT DOCUMENTS

| | | |
|---|---|---|
| JP | 2006136310 A | 6/2006 |
| WO | 2006/036130 A1 | 4/2006 |

OTHER PUBLICATIONS

Waterworth et al (In Vitro Cell. Dev. Biol.-Animal 2005. vol. 41, pp. 185-187).*
A. Waterworth, et al.; "A Novel Cell Array Technique for High-Throughput, Cell-Based Analysis", Vitro Cell. Dev.-Animal, 41 (2005), pp. 185-187.

* cited by examiner

*Primary Examiner* — Celine Qian
(74) *Attorney, Agent, or Firm* — Sughrue Mion, PLLC

(57) ABSTRACT

The present invention provides a pseudo-tissue for accuracy control comprising a nucleic acid or cells, a holding body for holding the nucleic acid or cells, and a protecting body for covering at least a part of the surface of the holding body so as to protect the holding body. A method for controlling accuracy by using the pseudo-tissue, and a method for manufacturing the pseudo-tissue are also disclosed.

5 Claims, 20 Drawing Sheets

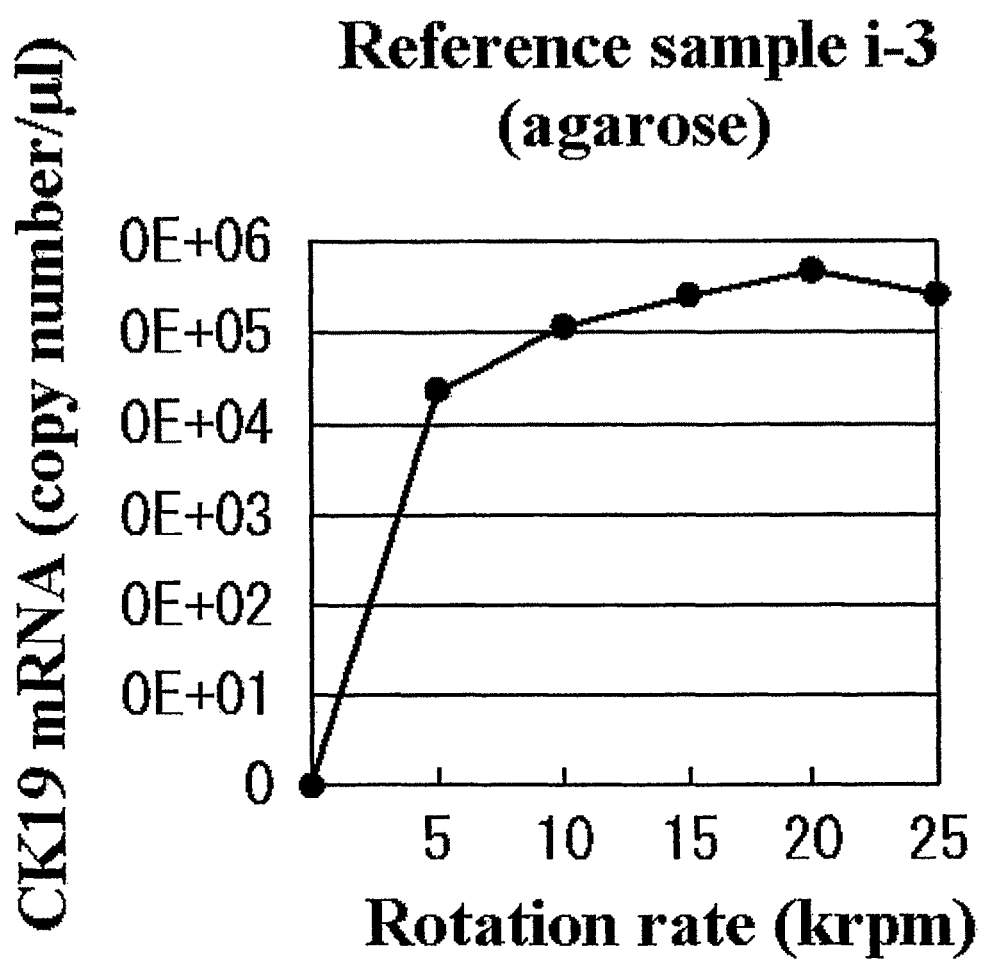

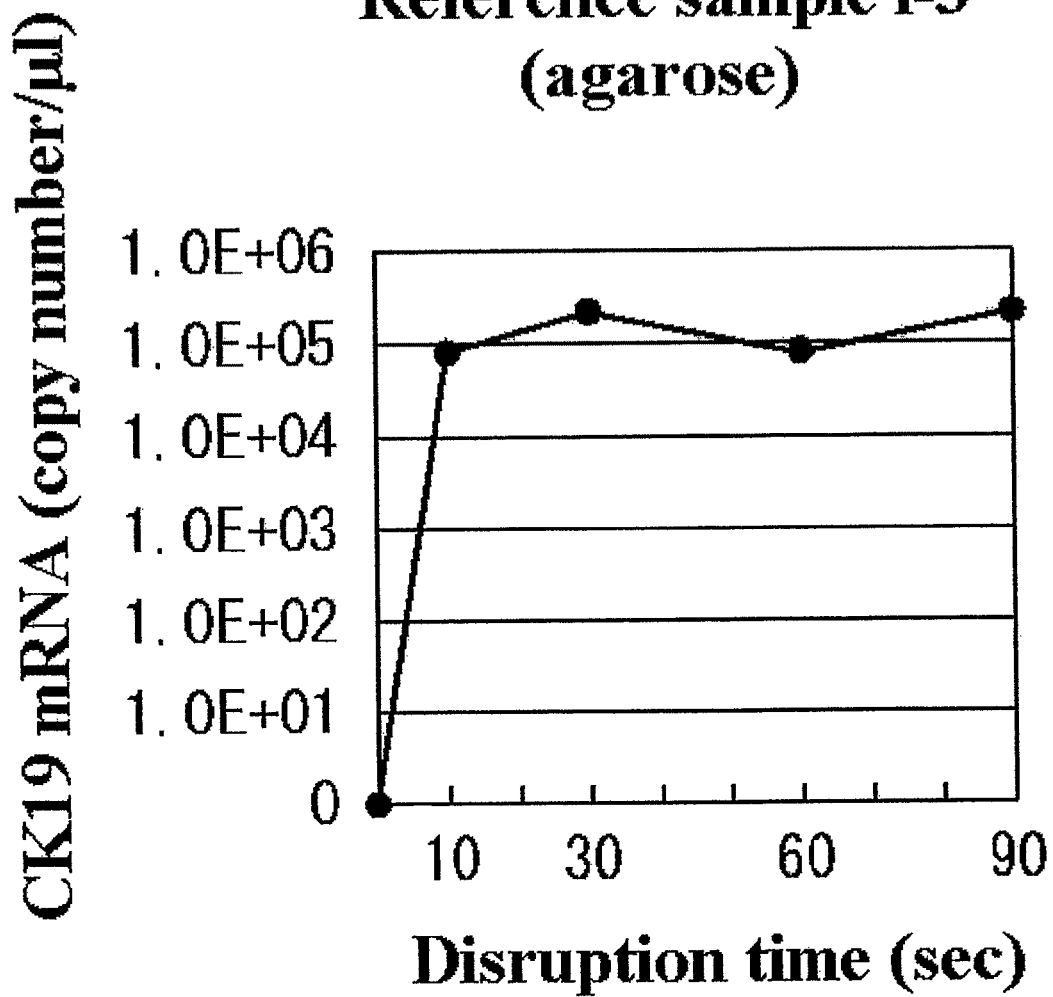

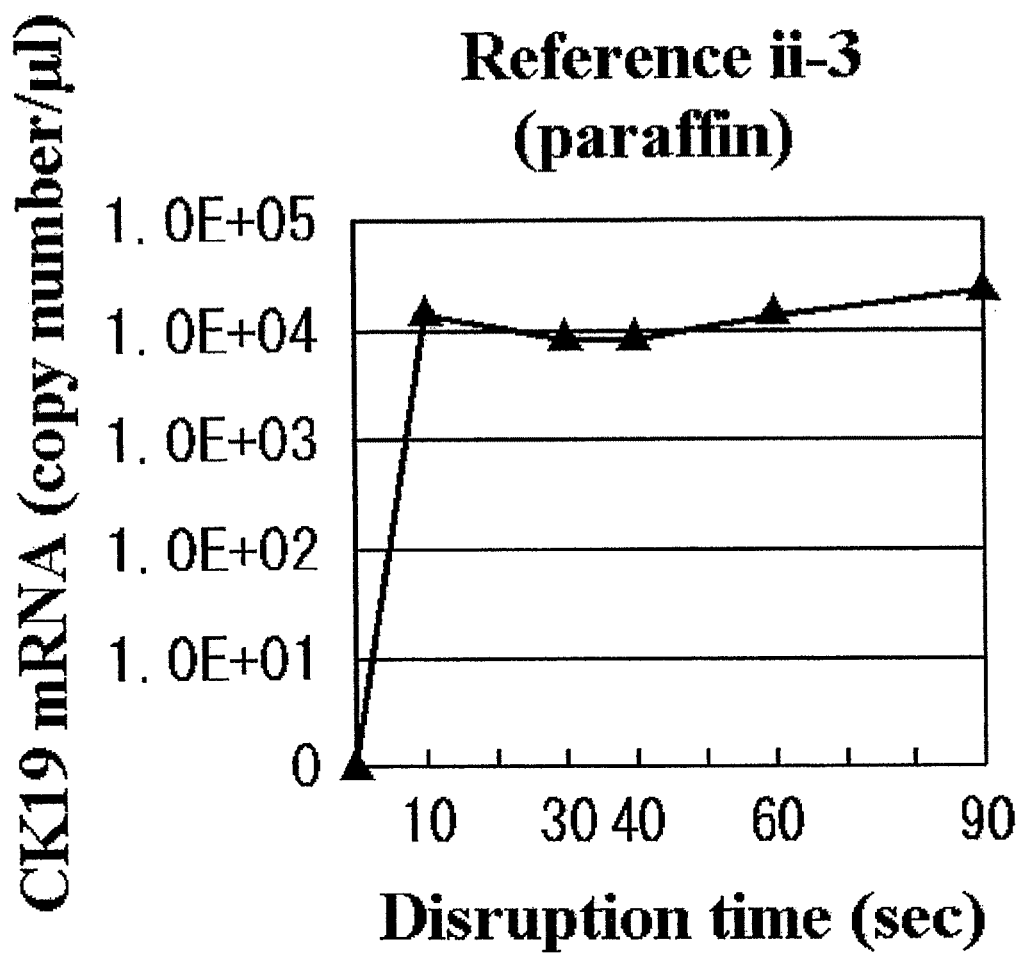

PSEUDO-TISSUE FOR ACCURACY CONTROL, METHOD FOR CONTROLLING ACCURACY BY USING THE SAME, AND METHOD FOR MANUFACTURING THE SAME

FIELD OF THE INVENTION

The present invention relates to a pseudo-tissue for accuracy control, a method for controlling accuracy by using the same, and a method for manufacturing the same.

BACKGROUND

In recent years, gene examination has rapidly spread in the field of clinical diagnosis. Gene examination is examination of the existence of mutations and karyotype's concerning genetic diseases for the clinical purpose by analyzing nucleic acids, chromosomes and the like. As an example of gene examination, there is an examination which determines whether or not a nucleic acid, derived from cancer cells, exists within a tissue excised from the living body. This examination process consists essentially of three primary steps: pretreatment, nucleic acid amplification, and detection.

Pretreatment step includes a variety of methods. By way of example, a reagent (buffer) for pretreatment is first added to cell mass such as lymph nodes, tumor mass and tissue fragments excised from the living body for the purpose of examination. Then, the excised tissue to which the reagent has been added is disrupted (homogenized), the resulting homogenate is centrifuged, and the target nucleic acid is extracted and purified, thereby giving a measurement sample. In the nucleic acid amplification step, the measurement sample is placed in a sample container, then reagents such as an enzyme, primers and the like are added thereto, and the target nucleic acid is amplified through the nucleic acid amplification reaction. In the detection step, the presence of the target nucleic acid in the excised tissue is judged or the concentration of the target nucleic acid is calculated, through measurements such as fluorescence measurement of the fluorescence-stained target nucleic acid or turbidity measurement of a by-product produced in proportion to the amplification.

In the gene examination described above, a variety of factors in each step affect the results of the measurement. Therefore, accuracy control for securing accuracy and reliability in each step is important in the field of gene examination. In the nucleic acid amplification step and in the detection step, accuracy control has been carried out by using a positive control and a negative control. In the pretreatment step, however, accuracy control has not been carried out.

Accordingly, the present inventors have previously proposed a substance for accuracy control, which can be used in accuracy control in pretreatment (US 2006/0084103). The substance for accuracy control in US 2006/0084103 is a pseudo-tissue for accuracy control comprising a nucleic acid or cells and a holding body that can hold the nucleic acid and cells. By using this pseudo-tissue for accuracy control, it becomes possible to conduct accuracy control in pretreatment of gene examination.

However, the substance for accuracy control in US 2006/0084103 has lower hardness than that of cell mass excised from the living body, and is thus easily disrupted and hardly exhibits the behavior of disruption similar to that of cell mass.

SUMMARY

The scope of the present invention is defined solely by the appended claims, and is not affected to any degree by the statements within this summary.

In view of these circumstances, the present invention has made, and the object of the present invention is to provide a pseudo-tissue for accuracy control that can exhibit the behavior of disruption similar to that of cell mass in pretreatment of gene examination, a method for controlling accuracy by using the same, and a method for manufacturing the same.

BRIEF DESCRIPTION OF THE DRAWINGS

FIG. 16(b) is a graph showing experimental results of reference sample i-3 in (1) in Example 3;

FIG. 17(b) is a graph showing experimental results of reference sample i-3 in (2) in Example 3;

FIG. 17(c) is a graph showing experimental results of reference sample ii-3 in (2) in Example 3;

DETAILED DESCRIPTION OF THE EMBODIMENT

Figure 1:
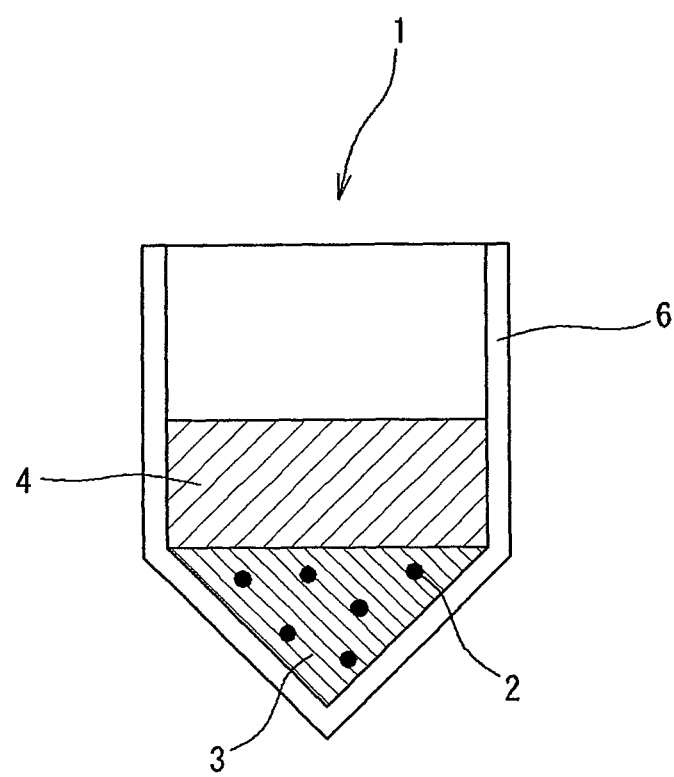
FIG. 1 is a schematic diagram showing the pseudo-tissue for accuracy control according to the present invention.

The pseudo-tissue for accuracy control (also referred to simply as "pseudo-tissue") in the embodiments of the invention refers to a pseudo-living tissue and is assumed to be specifically a lymph node excised from the living body and used in accuracy control in gene examination. This pseudo-tissue has a nucleic acid or cells, a holding body that holds the nucleic acid or cells, and a protecting body that covers at least a part of the surface of the holding body and protects the holding body.

The nucleic acid includes not only DNA and RNA but also artificial nucleic acids such as PNA, BNA, and analogs thereof. In addition, a nucleic acid that is encapsulated in a protein or the like, such as Armored RNA (U.S. Pat. No. 5,677,124) may be used as the nucleic acid in the present invention. A nucleic acid containing a nucleotide sequence of a gene encoding a tumor marker or a house keeping gene as described later can also be used. The origin of the nucleic acid is not particularly limited, and the nucleic acid may be extracted from cells or may be artificially synthesized.

The cells are not particularly limited as long as they are cells that contain a nucleic acid, and the cells are preferably cells containing a gene coding for a part or the whole of a substance to be examined in gene examination or cells containing mRNA etc. corresponding to the gene. Specific examples of the cells include cancer cells. In this case, the substance to be examined in gene examination includes tumor markers. Examples of such tumor markers include cytokeratin (CK), carcinoembryonic antigens, α-fetoprotein, tissue polypeptide antigens, immunosuppressive acid protein, α-fetoprotein, basic fetoprotein, PIVKA, DUPAN, elastase, SCC antigens, Pro GRP, neuron specific enolase, urinary NMP-22, prostatic acid phosphatase, γ-seminoprotein and the like.

The holding body is that which can hold the nucleic acid or cells (also referred to hereinafter as nucleic acid or the like), preferably that which is in a solid format room temperature, but upon heating to a certain temperature, breaks the solid form to make it fluidized. The holding body is a polymer having a melting point of 20 to 50° C., and can be formed for example from paraffin or agarose gel.

Paraffin refers generally to a mixture of nonvolatile and refined saturated hydrocarbons, and commercially available paraffin having various melting points and liquid paraffin that is liquid at normal temperature can be used alone or as a mixture of two or more thereof.

Agarose gel is a gel formed by adding a natural polymer agarose to a solvent such as water. Agarose is a polysaccharide whose main structure is made of D-galactose and 3,6-anhydro-L-galactose that are alternately connected, wherein the carbon at 1-position of D-galactose and the carbon at 4-position of 3,6-anhydro-L-galactose are connected through β-glycoside linkage, and the carbon at 1-position of 3,6-anhydro-L-galactose and the carbon at 3-position of D-galactose are connected through α-glycoside linkage. The origin of agarose is not particularly limited, and a variety of agarose contents in agarose ranging from a low to high degree of purification can be utilized.

In the pseudo-tissue, it is preferable that cells are held with a holding body consisting of a hydrophobic polymer and the cells are protected with vacuoles present around them. By the presence of vacuoles around the cell, the damage to the cell by the holding body can be blocked by the vacuoles. When the vacuoles are those of a cell storage solution or a buffer for washing cells, the cells can be positively protected by these vacuoles. The cell storage solution includes, for example, a mixture of fetal bovine serum (FBS) and 5 to 15% dimethyl sulfoxide (DMSO), a cell storage solution, pH 2.5 to 6, containing an agent for protection against freezing damage (preferably DMSO), Cell Banker (trade name) manufactured by Nippon Zenyaku Kogyo Co., Ltd., Ban Banker (trade name) manufactured by Lymphotec Co., Ltd., and an RNA stabilizer solution that is RNAlater (trade name) manufactured by Ambion. The buffer for washing cells includes, for example, a phosphate buffer (PBS) etc.

In the pseudo-tissue wherein cells are held with the holding body consisting of a hydrophobic polymer and the cells are protected by vacuoles present around them, the cells to be held with the holding body can be supplied with the holding body while liquid remains on the surface and/or inside of the cell, thereby converting the liquid into vacuoles around the cells. Then, this state of liquid remaining on the surface and/or inside of the cell can be formed without dehydration treatment of the cell, and for example, this state can be attained by washing a predetermined amount of cells with a cell storage solution or a washing buffer and then centrifuging the cells to remove a supernatant, followed by suspending the precipitated cells by adding a polymer constituting a holding body.

Usually, when tissue or the like is embedded in paraffin for observation under a microscope, water etc. in the tissue should be removed completely with alcohol so that paraffin can easily enter the tissue, and dehydration treatment is thus carried out, but in the present invention, the holding body is added without conducting dehydration treatment, thereby permitting liquid to remain on the surface and/or inside of the cell, and it is estimated that this liquid is converted into vacuoles around the cells thereby protecting the cells and simultaneously preventing the holding body from flowing in the cells.

In the pseudo-tissue of the present invention, the holding body is protected by a protecting body. This protecting body may be that which covers at least a part of the surface of the holding body and protects the holding body. The protecting body has hardness higher than that of the holding body, and can be formed from a polymer having a melting point higher than that of the holding body. In this case, the protecting body is preferably a hydrophobic polymer. If the protecting body is a hydrophobic polymer, a homogenizing reagent described later, in which the pseudo-tissue is dipped in a disrupting step, hardly flows in the pseudo-tissue, thus making the pseudo-tissue less liable to undergo the change in hardness caused by swelling. When the protecting body is paraffin, the protecting body is preferably paraffin having a melting point higher than that of paraffin used as the holding body.

In the pseudo-tissue, it is preferable that the protecting body is further covered with an outer membrane. The pseudo-tissue when structured by coverage with an outer membrane can be endowed with improved handleability and excellent storage stability. The outer membrane can be formed from gelatin or cellulose.

FIGS. 1, 3, 5 and 7 show the shapes of the pseudo-tissues of the present invention. The pseudo-tissues 1 shown in FIGS. 1 and 5 have cell 2, a holding body 3 that holds the cell 2, and a protecting body 4 that covers a part of the surface of the holding body 3 and protects the holding body 3. The pseudo-tissues 1 shown in FIGS. 3 and 7 have cell 2, a holding body 3 that holds the cell 2, and a protecting body 4 that covers the whole surface of the holding body 3 and protects the holding body 3. In the pseudo-tissue 1 in FIG. 7, a protecting body 4 is further covered with an outer membrane 5.

Figure 2:
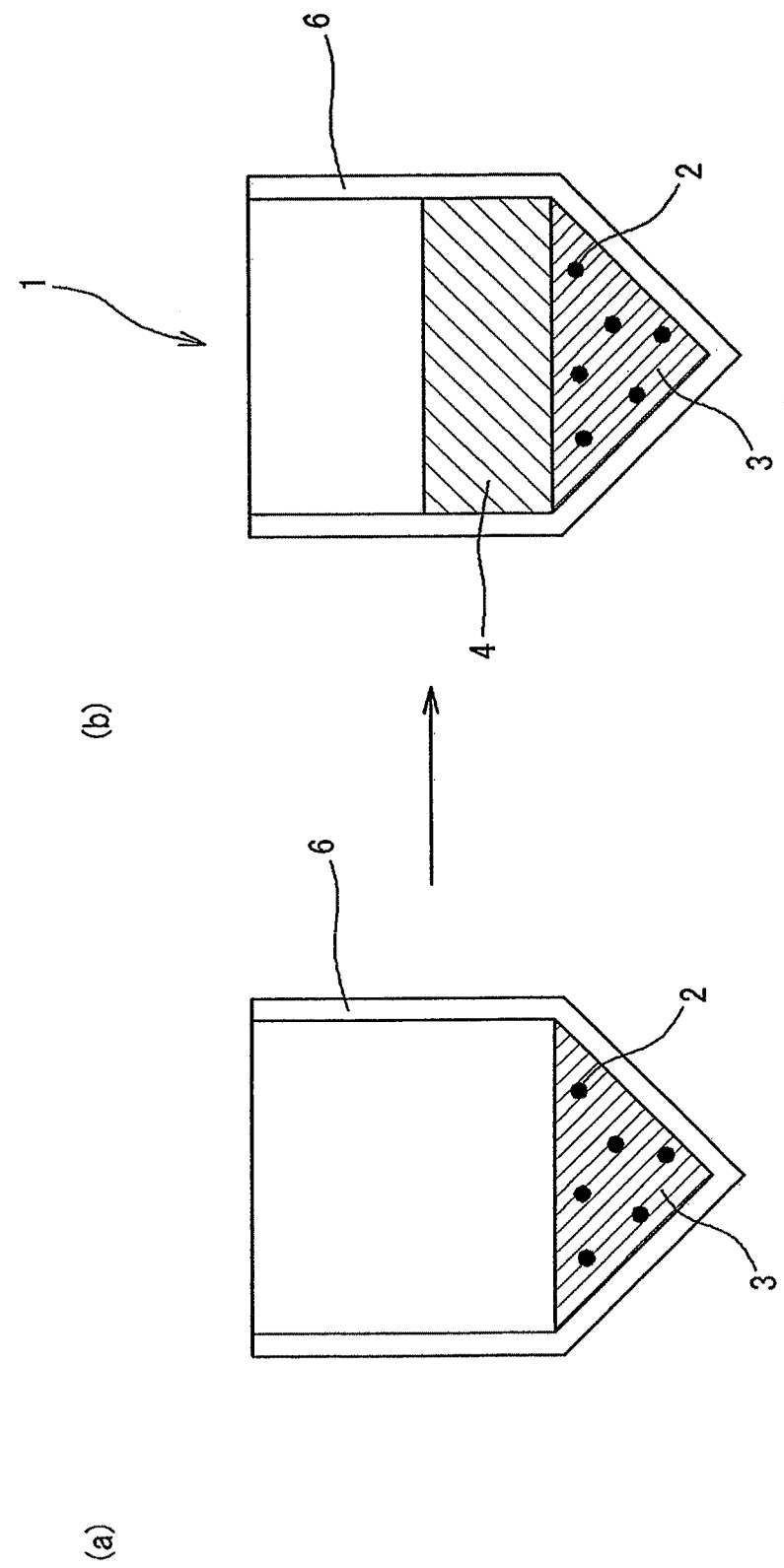
FIG. 2 is a schematic illustrative diagram showing a method for manufacturing the pseudo-tissue for accuracy control in FIG. 1.

FIG. 2 is a schematic illustrative diagram showing a method for manufacturing the pseudo-tissue in FIG. 1. The pseudo-tissue 1 in FIG. 1 can be produced for example by adding cells suspended in liquid paraffin (100 μl) constituting the holding body 3 to a 50-ml centrifuge tube 6, then adding 300 μl paraffin (mp. 42 to 44) constituting the holding body 3, to harden the holding body 3 (see (a) in FIG. 2), introducing 500 μl of a mixture of paraffin (mp. 44 to 46) and paraffin (mp. 48 to 50) at a ratio of 1:1 constituting the protecting body 4 onto the holding body 3 and hardening the mixture (see (b) in FIG. 2). The prepared pseudo-tissue 1 is stored at −20° C. in the centrifuge tube 6.

Figure 3:
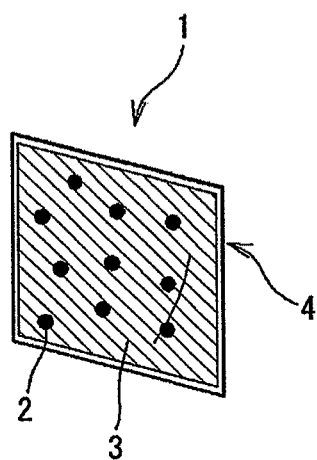
FIG. 3 is a schematic diagram showing the pseudo-tissue for accuracy control according to the present invention.
Figure 4:
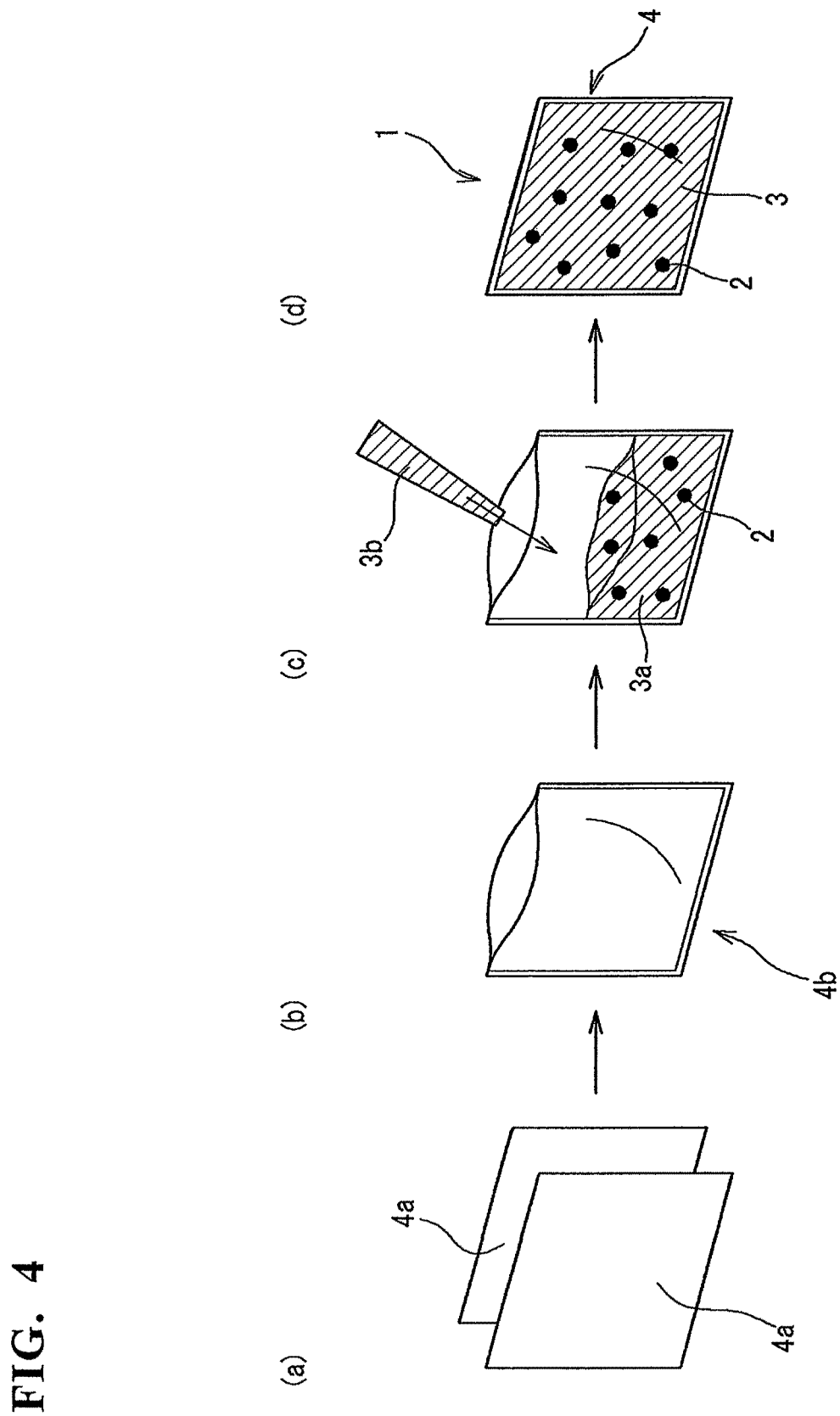
FIG. 4 is a schematic illustrative diagram showing a method for manufacturing the pseudo-tissue for accuracy control in FIG. 3.

FIG. 4 is a schematic illustrative diagram showing a method for manufacturing the pseudo-tissue 1 in FIG. 3. The pseudo-tissue 1 in FIG. 3 can be produced for example by laminating 2 sheets of about 1 cm×1 cm Parafilm 4a (manufactured by American National Can Company) constituting the protecting body 4 (see (a) in FIG. 4), sealing its 3 sides with a heat sealer to form a bag structure 4b (see (b) in FIG. 4), introducing cells 2 suspended in liquid paraffin 3a (100 μl) constituting the holding body 3, into the bag 4b formed from Parafilm, adding 300 μl of paraffin 3b (mp. 42 to 44) constituting the holding body 3 to harden the holding body 3, and sealing the opening of the bag 4b with a heat sealer (see (d) in FIG. 4). The prepared pseudo-tissue 1 is stored at −20° C.

Figure 5:
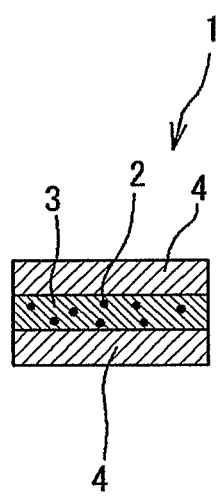
FIG. 5 is a schematic diagram showing the pseudo-tissue for accuracy control according to the present invention.
Figure 6:
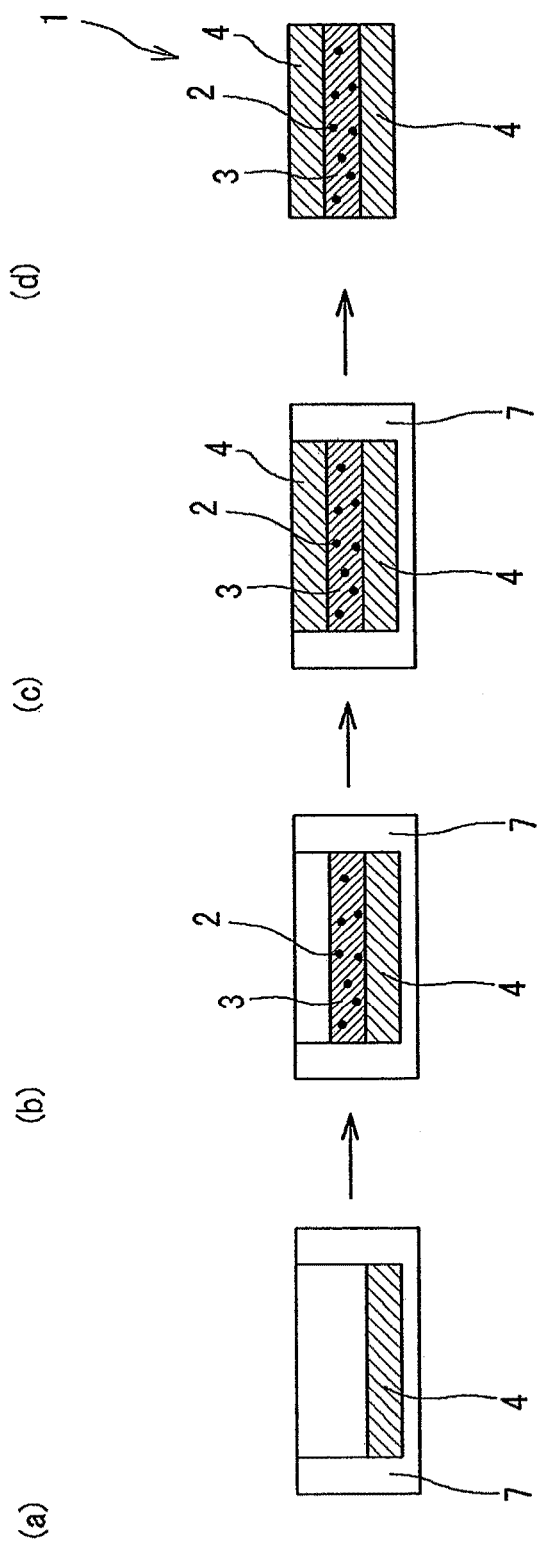
FIG. 6 is a schematic illustrative diagram showing a method for manufacturing the pseudo-tissue for accuracy control in FIG. 5.

FIG. 6 is a schematic illustrative diagram showing a method for manufacturing the pseudo-tissue 1 in FIG. 5. The pseudo-tissue 1 in the form of a sandwich in FIG. 5 can be produced for example by introducing 150 μl of a mixture of paraffin (mp. 44 to 46) and paraffin (mp. 48 to 50) at a ratio of 1:1 constituting the protecting body 4 into mold 7 and hardening the mixture (see (a) in FIG. 6), pouring cells 2 suspended in liquid paraffin (100 μl) constituting the holding body 3, onto the hardened paraffin layer 4, further adding 300 μl of paraffin (mp. 42 to 44) constituting the holding body 3, hardening the paraffin to form a layer of the holding body 3 (see (b) in FIG. 6), introducing 150 μl of a mixture of paraffin (mp. 44 to 46) and paraffin (mp. 48 to 50) at a ratio of 1:1 constituting the protecting body 4 onto the layer of the protecting body 3, to harden the mixture (see (c) in FIG. 6), and then removing the product from the mold 7 (see (d) in FIG. 6). The prepared pseudo-tissue 1 is stored at −20° C.

The shape of the pseudo-tissue 1 described above is merely illustrative and not intended to be limitative. In the method for manufacturing the same, paraffin was used as the holding body, and paraffin having a melting point higher than that of paraffin used as the holding body was used as the protecting body, but agarose etc. may be used as the holding body, and a material other than paraffin can be used as the protecting body.

Hereinafter, accuracy control in pretreatment by nucleic acid amplification and nucleic acid detection using the accuracy control method of the present invention is described.

Accuracy control in pretreatment by nucleic acid amplification and nucleic acid detection comprises a step of homogenizing a pseudo-tissue for accuracy control, a step of amplifying a nucleic acid contained in the homogenized pseudo-tissue for accuracy control, a step of measuring the concentration of the nucleic acid derived from the pseudo-tissue for accuracy control, by detecting the amplified nucleic acid, and a step of comparing the measured value of nucleic acid concentration with a standard value.

In this accuracy control method, the measured value of nucleic acid concentration can be compared with a standard value in the comparison step, to determine whether the homogenizing step, the amplification step and the measurement step have been suitably conducted.

According to this accuracy control method, accuracy control is carried out by using the pseudo-tissue for accuracy control according to the present invention. In the pseudo-tissue for accuracy control according to the present invention, the holding body in addition to the holding body is disrupted in the homogenizing step. Accordingly, disruption of the pseudo-tissue of the present invention is more difficult than that of the pseudo-tissue for accuracy control having a holding body only and described in US 2006/0084103. It follows that, in disruption treatment as pretreatment of gene examination, the pseudo-tissue for accuracy control according to the present invention can show the behavior of disruption similar to that of cell mass excised from the living body. The reliability of accuracy control in gene examination can thereby be further improved.

<Establishment of Standard Value>

Now, establishment of the standard value is specifically described.

A nucleic acid solution that contains a nucleic acid, or a cell suspension that contains cells, is mixed with a reagent that contains a buffer agent (hereinafter referred to as homogenizing reagent), to prepare a control sample α. When the cells are contained in the solution, a mixture of the cell suspension and the homogenizing reagent will be sufficiently homogenized as the control sample α. The number of cells in the cell solution is counted in advance by using a cell counting board (for example, counting chamber 8100105, made by AS ONE CORPORATION) or a cell number counting device (for example, particle number counting analyzer CDA-500, made by Sysmex Corporation).

Next, pseudo-tissue α is prepared by using the same amount of the same nucleic acid solution or cell suspension that is used for the preparation of the control sample α.

In preparation of the pseudo-tissue α, a commercial capsule for example serving as an outer membrane is first prepared. A polymer constituting the protecting body is introduced into the body of the capsule and then hardened. Then, an opening is formed in the hardened protecting body. The same amount of the same nucleic acid solution or cell suspension that is used for the preparation of the control sample α, and a polymer constituting the holding body, are uniformly mixed with each other to prevent uneven distribution of the nucleic acid or cells, and the mixed liquid is injected into the opening and then hardened. Then, a polymer etc. constituting the protecting body is also introduced into a cap of the capsule and then hardened. Then, the body is capped with the cap. In this manner, the pseudo-tissue α having a nucleic acid or cells, a holding body that holds the nucleic acid or cells, a protecting body that protects the holding body, and an outer membrane covering the protecting body is obtained.

The pseudo-tissue α is subjected to the same pretreatment as in gene examination. First, a homogenizing reagent is added to the pseudo-tissue α. The amount of the homogenizing reagent added is adjusted so that the volume of a mixture of the pseudo-tissue α and the homogenizing reagent becomes equal to the volume of the control sample α. The mixture of the pseudo-tissue α and the homogenizing reagent is homogenized to prepare a homogenate. Then, the homogenate obtained from the pseudo-tissue α is centrifuged, and the resulting supernatant is accommodated in another container. Hereinafter, this supernatant is referred to as measurement sample α.

Then, the control sample α and the measurement sample α are subjected to nucleic acid amplification and nucleic acid detection.

For nucleic acid amplification, a known nucleic acid amplification method of amplifying a target nucleic acid by using a DNA and RNA contained in the control sample α and the measurement sample α can be utilized. Specific examples of the nucleic acid amplification method include PCR, RT-PCR, LAMP, RT-LAMP, TMA (Transcription Mediated Amplification), NASBA, 3SR, SDA (Strand Displacement Amplification), ICAN (Isothermal and Chimeric primer-initiated Amplification of Nucleic acids), RCA (Rolling Circle Amplification), INVADER, CPT (Cycling Probe Technology), and PALSAR methods. Particularly, PCR, RT-PCR, LAMP and RT-LAMP methods are preferable.

The nucleic acid detection method is not limited and any known nucleic acid detection methods can be used in nucleic acid detection. For example, when LAMP or RT-LAMP method is used, insoluble materials such as magnesium pyrophosphate are formed as the nucleic acid amplification advances. Accordingly, 1) the turbidity of the supernatant of the reaction solution is confirmed with the naked eye, 2) the turbidity is measured through the measurement of the absorbance of the reaction solution or the intensity of scattered light, or 3) the reaction solution is filtered through a colored filter so that residues on the filter can be inspected, and thereby, the target nucleic acid can be detected (US2003/129632). In addition, in the case where the nucleic acid amplification is carried out under the existence of a fluoro-chrome, which is a double strand intercalator, such as ethidium bromide, SYBR GREEN I or Pico Green, the target nucleic acid detection can be carried out through the measurement of fluorescent light of the reaction solution. In the measurement of the turbidity or in the measurement of the fluorescent light, an increase in the turbidity or in the intensity of fluorescent light can be observed together with an increase in the product by nucleic acid amplification. If this increase is monitored in real time, an increase in the amount of nucleic acid and an increase in the turbidity or in the intensity of fluorescent light can be traced at the same time in a closed system.

In the case where the nucleic acid detection is carried out through turbidity measurement or fluorescence measurement, the measurement sample α and the control sample α are measured respectively for the concentration of the target nucleic acid contained therein. Then, the measured concentration of the target nucleic acid in the measurement sample α and the measured concentration of the target nucleic acid in the control sample α (hereinafter referred to as control value α) are compared. When these show equal values or close values (for example, in the case where a value obtained by measuring the concentration of the target nucleic acid of the measurement sample α shows a value that is 70% or more of the control value α, preferably 80% or more), it can be assumed that the target nucleic acid that is contained in the measurement sample α originating from pseudo-tissue α was effectively extracted through homogenization, and this value obtained by measuring the concentration of the target nucleic acid in the measurement sample α can be referred to as standard value α.

In the case where an increase in the turbidity or in the intensity of fluorescent light is monitored in real time, the time required for the nucleic acid that is contained in the measurement sample α to start being amplified (amplification starting time) and the amplification starting time of control sample α (hereinafter referred to as control value αt) are compared. In the case where these show equal or close values, it can be assumed that the target nucleic acid that is contained in measurement sample α was effectively extracted through homogenization, and the starting time thereof can be referred to as standard value αt.

In the case where the nucleic acid detection is carried out through visual inspection, the turbidity of the control sample α and the turbidity of the measurement sample α are compared, and thereby, whether or not pretreatment was precisely carried out on the measurement sample α can be confirmed.

<Accuracy Control of Pretreatment by Standard Value α or αt>

Next, an accuracy control method by the standard value α or αt is described.

First, a pseudo-tissue β is prepared for accuracy control. Pseudo-tissue β is a pseudo-tissue of the same lot as the above described pseudo-tissue α. Pretreatment is carried out on pseudo-tissue β, in the same manner as the pretreatment that has been carried out on pseudo-tissue α, and thereby, the measurement sample β is prepared. The same operations as in the nucleic acid amplification and the nucleic acid detection that have been carried out on the above described measurement sample α are carried out on the measurement sample β. Then, the concentration of the target nucleic acid and/or the amplification starting time of the measurement sample β is measured. In the case where the value obtained by measuring the concentration of the target nucleic acid or the amplification starting time of the measurement sample β is equal or close to the above described standard value α or αt, it can be confirmed that the pretreatment that has been carried out on pseudo-tissue β was appropriate.

Here, at least one step from among the above described pretreatment, the nucleic acid amplification and the nucleic acid detection may be automatically carried out by a unit. A nucleic acid amplification detecting unit, for example, can be cited as a unit that automatically carries out nucleic acid amplification or nucleic acid detection. A nucleic acid amplification detecting unit which helps in the diagnosis of cancer metastasis conducted on excised tissue during a cancer operation can be cited as an example of a nucleic acid amplification detecting unit. This unit allows mRNA within the excised tissue to be used as a template for the reverse transcription from mRNA to cDNA in accordance with an RT-LAMP (reverse transcription loop mediated isothermal amplification, Eiken Chemical Co., Ltd.) method, and this cDNA is amplified and the turbidity of the solution which increases together with the amplification measured, and thereby, the starting time of the amplification and the copy number of mRNA within the excised tissue can be calculated in the unit.

Figure 8:
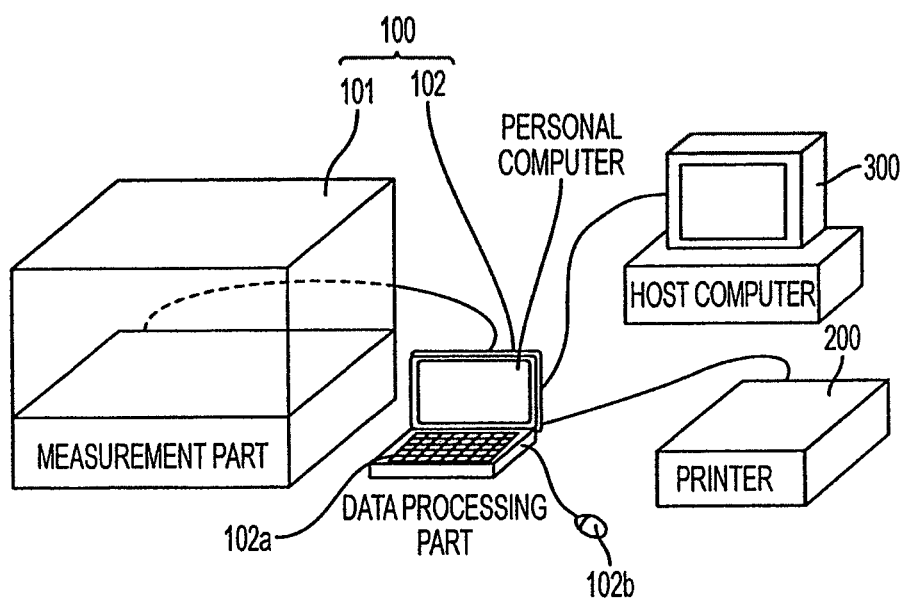
FIG. 8 is a perspective view showing the entire configuration of a nucleic acid amplification detecting unit and its peripheral equipments.
Figure 9:
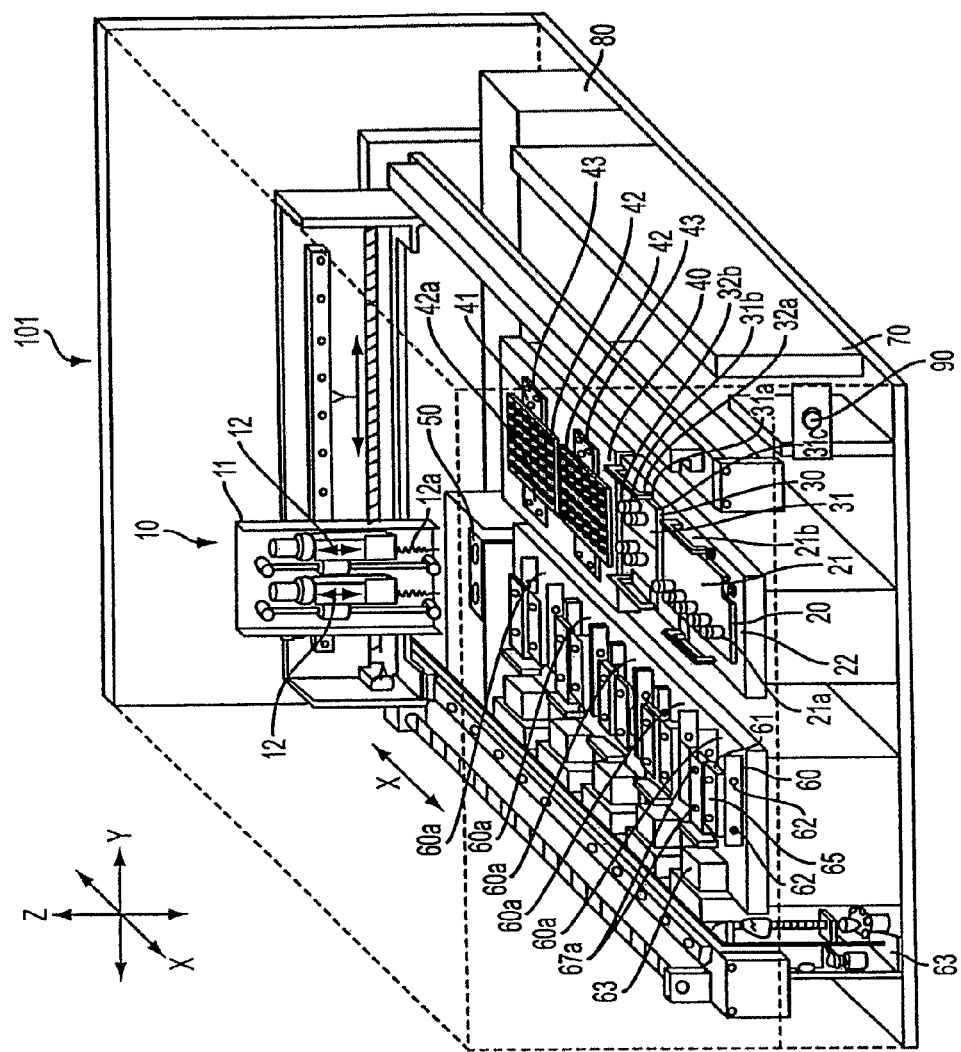
FIG. 9 is a diagram showing the entire configuration of the determining part of the nucleic acid amplification detecting unit.

Hereinafter, the nucleic acid amplification detecting unit is described by reference to the Drawings. This nucleic acid detecting unit allows the content of nucleic acid from a cancer marker (for example, cytokeratin 19) in the tissue that has been excised from a living organism to be quantified. FIG. 8 is a perspective view showing the entire configuration of a nucleic acid amplification detecting unit and its peripheral equipments. FIG. 9 is a diagram showing the entire configuration of the measurement part of the nucleic acid amplification detecting unit shown in FIG. 8.

First, the entire configuration of a nucleic acid amplification detecting unit and its peripheral equipments is described by reference to FIG. 8. The nucleic acid amplification detecting unit 100, as shown in FIG. 8, is formed of a the measurement part 101 and a data processing part 102 that is connected to the measurement part 101 through a communication line. The data processing part 102 consists of a personal computer including a keyboard 102a and a mouse 102b. Printer 200 as a peripheral equipment and a host computer 300 are connected via a communication line to the data processing part 102. The printer 200 is disposed for printing graphic data, text data etc. Measurement data are outputted from the data processing part 102 into the host computer 300.

As shown in FIG. 9, a measurement part 101 includes a delivering mechanism 10, a sample container setting part 20, a reagent container setting part 30, a chip setting part 40, a chip disposal part 50 and a reaction detecting part 60 made of five reaction detecting blocks 60a. As shown in FIG. 9, the measurement part 101 controls the unit by means of a microcomputer, and incorporates a control part 70 for controlling input into/output from the outside of the unit, and a power supply part 80 for supplying power to the entirety of the unit including control part 70. In addition, an emergency shutdown switch 90 is placed at a predetermined point in front of the measurement part 101.

The sample container setting part 20, the reagent container setting part 30 and chip setting part 40 are placed in the direction of the X axis. In addition, sample container setting part 20 is placed on the front side of the unit, and reagent container setting part 30 is placed on the rear side of the unit. In addition, five reaction detecting blocks 60a and chip disposal part 50 are placed in the direction of the X axis at points that are at a predetermined distance from sample container setting part 20, reagent container setting part 30 and chip setting part 40 in the direction of the Y axis. That is, sample container setting part 20, reagent container setting part 30, chip setting part 40, chip disposal part 50 and the five reaction detecting blocks 60a are arranged in square form (rectangular form).

In addition, delivering mechanism 10 includes an arm part 11 which is moveable in the direction of the X and Y axes (on a plane), and two syringe parts 12 which are independently moveable in the direction of the Z axis (vertically) relative to arm part 11. The two syringe parts 12 are respectively provided with a nozzle part 12a, at the end of which a pipette chip can be mounted.

In addition, as shown in FIG. 9, a sample container setting base 21 having five sample container setting holes 21a and handles 21b is removably engaged in a recess of sample container setting part 20. The five sample container setting holes 21a in sample container setting base 21 are provided at predetermined intervals in single column form in the direction of the X axis. Sample containers 22 that contain measurement samples that have been prepared by pretreatment excised tissue and/or pseudo-tissue are set in the five sample container setting holes 21a of this sample container setting base 21.

A reagent container setting base 31 having two primer reagent container setting holes 31a, two enzyme reagent container setting holes 31b and handles 31c is removably engaged in a recess of reagent container setting part 30. The two primer reagent container setting holes 31a and the two enzyme reagent setting holes 31b of reagent container setting base 31 are respectively provided at a predetermined distance in the direction of the Y axis. Two primer reagent containers 32a, which contain two types of primer reagents, and two enzyme reagent containers 32b, which contain enzyme reagents that correspond to these two types of primer reagents, are set in primer reagent container setting holes 31a and enzyme reagent setting holes 31b of this reagent container setting base 31, respectively. Here, primer reagent container 32a which contains a primer reagent that corresponds to mRNA of cytokeratin 19 (CK19) and enzyme reagent container 32b which contains an enzyme reagent of CK19 mRNA are placed in primer reagent container setting hole 31a and enzyme reagent container setting hole 31b on the left side when viewed from the front. In addition, primer reagent container 32a which contains a primer reagent of mRNA of β-actin as an internal reference material, and enzyme reagent container 32b which contains an enzyme reagent of β-actin mRNA are placed in primer reagent container setting hole 31a and enzyme reagent container setting hole 31b on the right side when viewed from the front. The internal reference material is not limited to actin, and mRNA of other housekeeping genes and the like can also be used (US 2005/164190).

Two racks 42 having containing holes 42a where thirty-six pipette chips 41 can be contained are respectively detachably engaged in two recesses of chip setting part 40. In addition, two removing buttons 43 are provided to chip setting part 40. Racks 42 become of a removable state by pressing these removing buttons 43.

As shown in FIG. 9, each reaction detecting block 60a of reaction detecting part 60 is formed of a reaction part 61, two turbidity detecting parts 62 and a lid closing mechanism 63. Each reaction part 61 is provided with a detection cell 65. Lid closing mechanism 63 has a function of mounting a cell part 67a in detection cell 65.

The procedure of the operation and the operation of the unit in the case where nucleic acid detection is carried out by the nucleic acid amplification detection unit described above are concretely described. Hereinafter, the procedure and operation are described by reference to a pseudo-tissue having cells, a holding body that holds the cells, a protecting body that covers at least a part of the surface of the holding body and protects the holding body, and an outer membrane that covers the protecting body.

<Calculation of Standard Value γ>

First, a cell suspension that contains cells which are considered to include CK19 mRNA and a homogenizing reagent are mixed and then sufficiently homogenized to prepare a reference sample γ. Here, the number of cells in the cell suspension is counted in advance.

Next, the same amount of the same cell suspension as that which is used for the manufacture of control sample γ is used to prepare a pseudo-tissue γ in the same manner as the preparation of the above described pseudo-tissue α.

A homogenizing reagent is added to pseudo-tissue γ. The added amount of homogenizing reagent is adjusted so that the volume of the mixture of pseudo-tissue γ and the homogenizing reagent becomes equal to the volume of control sample γ. The mixture of pseudo-tissue γ and the homogenizing reagent is homogenized so as to prepare a homogenate. The homogenate obtained from pseudo-tissue γ is centrifuged, and the supernatant is contained in another container. Hereinafter, this supernatant is referred to as measurement sample γ.

Containers which contain control sample γ and measurement sample γ are respectively set in sample container setting holes 21a of sample container setting base 21. In addition, a primer reagent container 32a which contains the primer reagent of CK19 mRNA, and an enzyme reagent container 32b which contains the enzyme reagent of CK19 mRNA are set in primer reagent container setting hole 31a and enzyme reagent container setting hole 31b, on the left side when viewed from the front.

In addition, a primer reagent container 32a which contains the primer reagent of β actin mRNA, and an enzyme reagent container 32b which contains the enzyme reagent of γ-actin mRNA are set in primer reagent container setting hole 31a and enzyme reagent container setting hole 31b, on the right side when viewed from the front.

In addition, two racks 42, each of which contains thirty-six disposable pipette chips 41, are engaged in the recesses of chip setting part 40. Furthermore, two cell parts 67a of detection cells 65 are set in two detection cell setting holes 61a of the reaction part 61 of each reaction detecting block 60a.

Then, keyboard 102a of the data processing part 102, and mouse 102b, shown in FIG. 8, are used to resister measurement items, sample ID etc., and then the operation of the measurement part 101 is started by the keyboard 102a or mouse 102b.

When the operation of the measurement part 101 is started, arm part 11 of delivering mechanism 10 is moved from the initial position to chip setting part 40, and in the chip setting part 40, two syringe parts 12 of delivering mechanism 10 move in the downward direction, and thereby, the ends of nozzle parts 12a of the syringe parts 12 are pressed into the upper openings of the pipette chips 41, and pipette chips 41 are thus automatically mounted on the ends of nozzle parts 12a of the syringe parts 12. Then, after the two syringe parts 12 have moved upwards, arm part 11 of delivering mechanism 10 is moved in the direction of the X axis, toward a point above the two primer reagent containers 32a which contain the primer reagents of CK19 mRNA and β actin mRNA, and which are set in sample container setting holding body 31. Then, the two syringe parts 12 are moved in the downward direction, and thereby, the ends of the respective pipette chips 41 are inserted in through the liquid surface of the primer reagents of CK19 mRNA and β-actin mRNA within the two primer reagent containers 32a, and the respective primer reagents are drawn into pipette chips 41 by a pump in the syringe part 12.

After the primer reagents have been drawn into the pipette chips and the two syringe parts 12 are moved upward, arm part 11 of delivering mechanism 10 is moved to a point above a reaction detecting block 60a positioned in the backmost side (backside of the front of the unit). In this case, the arm part 11 of delivering mechanism 10 is moved so as not to pass over the other reaction detection blocks 60a at the second to fifth positions from the back. Then, in the reaction detection block 60a in the backmost side, the two syringe parts 12 are moved in the downward direction, and thereby, two pipette chips 41, which are mounted on nozzle parts 12a of the two syringe parts 12, are respectively inserted into cell parts 67a of detection cells 65, and the primer reagents of CK19 mRNA and β actin mRNA are respectively discharged into the two cell parts 67a by using the pump in the syringe part 12 (primer reagent dispensing processing).

After the discharge of the primer reagents, the two syringe parts 12 are moved upward, and arm part 11 of delivering mechanism 10 is moved in the direction of the X axis toward a point above chip disposal part 50. In chip disposal part 50, pipette chips 41 are disposed.

Next, arm part 11 of delivering mechanism 10 is again moved to chip setting part 40, and the same operation as described above is carried out in chip setting part 40, and thereby, two new pipette chips 41 are automatically mounted on the ends of nozzle parts 12a of the two syringe parts 12. Then, arm part 11 of delivering mechanism 10 is moved in the direction of the X axis toward a point above the two enzyme reagent containers 32b which respectively contain the two enzyme reagents of CK19 mRNA and β actin mRNA, and which are set in reagent container setting base 31. After that, the two syringe parts 12 are moved in the downward direction, and thereby, the two enzyme reagents of CK19 mRNA and β actin mRNA within the two enzyme reagent containers 32b are drawn into the syringe parts 12, which are then moved in the upward direction. Then, arm part 11 of delivering mechanism 10 is moved to a point above a reaction detecting block 60a, and after that, the two enzyme reagents of CK19 mRNA and β actin mRNA are discharged into the two cell parts 67a of detection cells 65, respectively (enzyme reagent dispensing processing). After the discharge of the enzyme reagents, arm part 11 of delivering mechanism 10 is moved to a point above chip disposal part 50, and then, pipette chips 41 are disposed.

Next, arm part 11 of delivering mechanism 10 is again moved to chip setting part 40, and after that, two new pipette chips 41 are automatically mounted on the ends of nozzle parts 12a of the two syringe parts 12. Then, arm part 11 of delivering mechanism 10 is moved in the direction of the X axis toward a point above the two sample containers 22 which respectively contain control sample γ and measurement sample γ that are set in sample container setting base 21, and after that, control sample γ and measurement sample γ are respectively drawn into pipette chips 41.

When control sample γ and measurement sample γ are respectively discharged into two cell parts 67a of detection cells 65, the mixtures within the two cell parts 67a are mixed through the automated pipetting of the two syringe parts 12. After this, arm part 11 of delivering mechanism 10 is moved to a point above chip disposal part 50, and then, pipette chips 41 are disposed.

After the respective reagents, control sample γ and measurement sample γ have been respectively contained within the above described cell parts 67a, and the lids of cell parts 67a of detection cells 65 have been closed by means of lid closing mechanism 63, and then a Peltier module in the reaction part 61 is used to heat the liquids within detection cells 65 from about 20° C. to about 65° C., and thereby, cDNA (hereinafter referred to CK19 cDNA) is amplified using the target nucleic acid (CK19 mRNA) as a template, by means of the above described RT-LAMP.

Then, a white, cloudy liquid of magnesium pyrophosphate that is created together with the amplification is monitored in real time through measurement of turbidity. Concretely speaking, cell parts 67a of detection cells 65 (measurement data acquisition part) are irradiated, via a light irradiation groove of the reaction part 61, with light having a diameter of about 1 mm from an LED light source (not shown) at the time of the amplification reaction. The light that has been irradiated is received by a photodiode light receiving part (not shown), and thereby, the turbidity of the liquid within cell parts 67a of detection cells 65 at the time of the amplification reaction is monitored in real time (detection processing). The measurement data of CK19 measured by a photodiode light receiving part (measurement data acquisition means) of the turbidity detection part 62 is sent via a transmission part (not shown) of the measurement part 101 to the data processing part 102.

Figure 10:
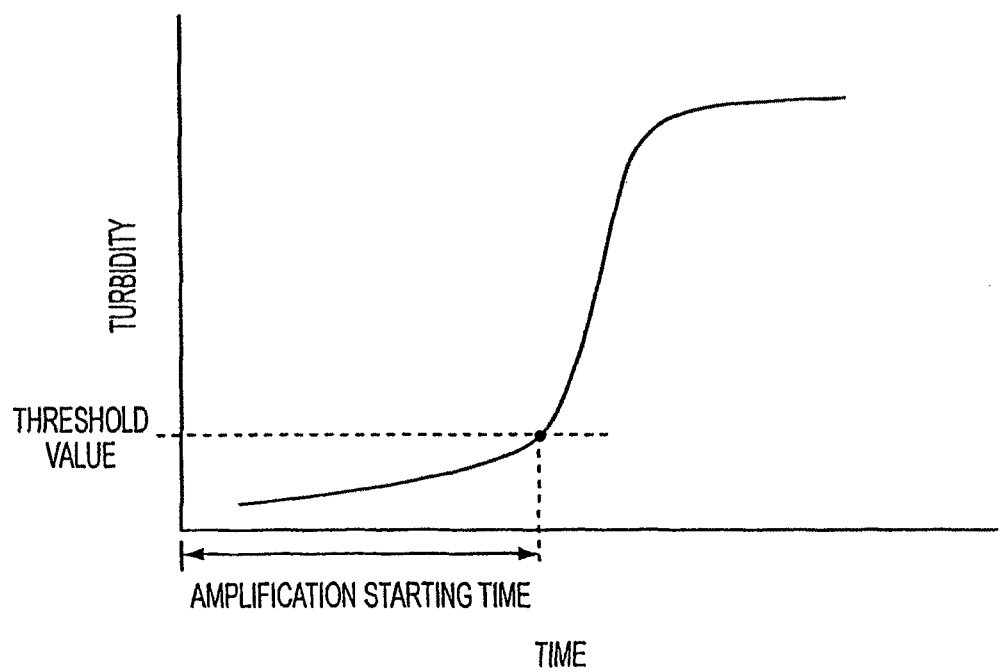
FIG. 10 is a graph showing the relationship between the amplification starting time and turbidity.
Figure 11:
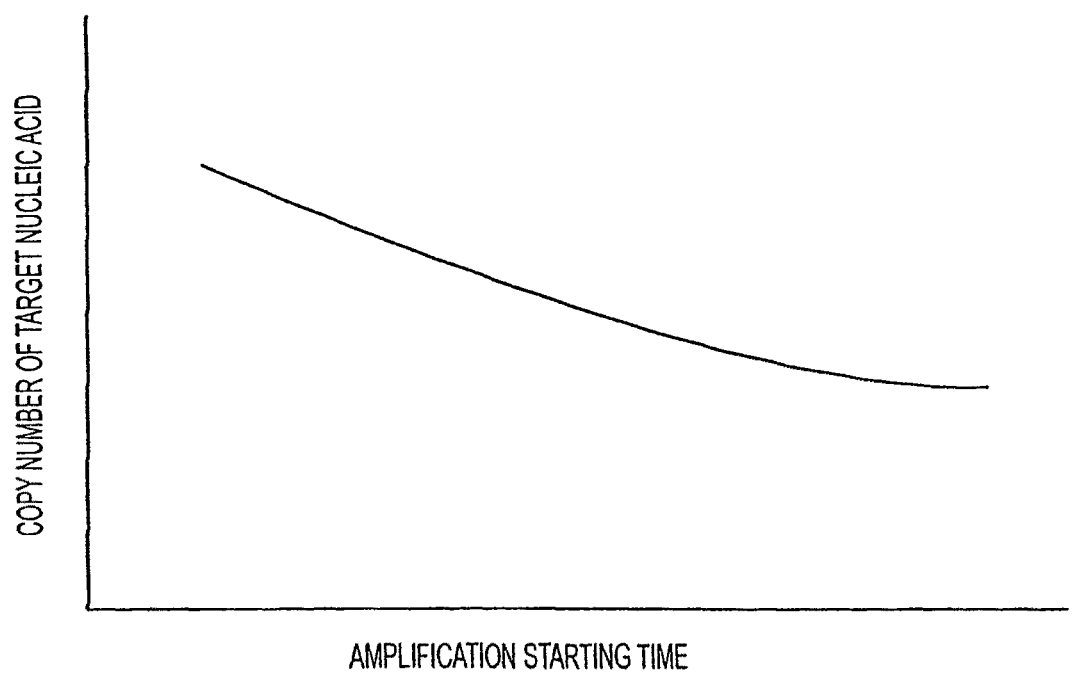
FIG. 11 is a graph showing a calibration curve showing the relationship between the amplification starting time and the copy number of target nucleic acid.

As a result, measurement data on CK19 as shown in FIG. 10 where time is shown on the abscissa and turbidity on the ordinate can be obtained in the data processing part 102. Then, the time elapsed until an amplification product of CK19 cDNA in the sample is rapidly increased (amplification starting time) is measured. The concentrations of CK19 mRNA (copy number/μL) contained in the control sample γ and the measurement sample γ are respectively determined on the basis of a calibration curve previously prepared from the measurement results of CK19 calibrator as shown in FIG. 11. The calibration curve shown in FIG. 11 is a curve wherein the amplification starting time is shown on the abscissa and the copy number of the target nucleic acid (copy number/μL) on the ordinate, and a shorter amplification starting time is indicative of a higher concentration of the target nucleic acid.

The concentration of CK19 mRNA in the control sample γ, as determined by turbidity measurement, is referred to as control value γ. In the case where the concentration of CK19 mRNA in the measurement sample γ is equal to or in the proximity of the control value γ, it can be assumed that CK19 mRNA contained in the measurement sample γ could be effectively extracted through homogenization, and this concentration of CK19 mRNA can be used as the standard value γ.

<Accuracy Control Method Based on the Standard Value γ>

Now, an accuracy control method based on the standard value γ is described.

Pseudo-tissue δ is prepared for accuracy control. The pseudo-tissue δ is a pseudo-tissue of the same lot as the above described pseudo-tissue γ. Pretreatment of the pseudo-tissue δ, such as homogenization, centrifugation, and recovery of a supernatant, is carried out in the same manner as in pretreatment of pseudo-tissue γ. The supernatant of the pseudo-tissue δ is subjected to the same operation as in nucleic acid amplification and nucleic acid detection for the measurement sample γ as described above, and the concentration of CK19 mRNA in the supernatant of the pseudo-tissue δ is measured. In the case where the concentration of CK19 mRNA in the supernatant of the measurement sample δ is equal to or close to the standard value γ, it can be confirmed that the treatment carried out on the pseudo-tissue δ was appropriate.

EXAMPLES

Example 1

In Example 1, reference sample i wherein target nucleic acid-containing cells were held with a holding body using agarose gel or paraffin was prepared, and then subjected to predetermined treatment such as homogenization to measure the copy number of CK19 mRNA contained in the cells, thereby confirming whether the nucleic acid can be extracted and amplified from the reference sample.

<Preparation of Reagents>

A homogenizing reagent, a reaction solution, an enzyme reagent and a primer reagent were prepared in the following manner.

A homogenizing reagent containing the following reagents was prepared.
200 mM glycin-HCl, pH 3.0 (both glycine and HCl were manufactured by Wako Pure Chemical Industries, Ltd.)
5% Brij 35 (Sigma)
0.05% KS-538 (manufactured by Shin-Etsu Chemical Co., Ltd.)

The concentrations described above indicate the concentrations in the reagent.

13.97 µl of a reaction solution was prepared by mixing the following components:

| | |
|---|---|
| 750 mM Tris buffer, pH 8.0 | 1.00 µl |
| 10× Thermopol buffer (manufactured by New England Biolaboratory) | 2.50 µl |
| 10 mM dNTPs | 2.00 µl |
| 100 mM MgSO$_4$ | 0.75 µl |
| 100 mM dithiothreitol | 1.25 µl |
| 2% Tergitol (manufactured by Sigma Aldrich Japan) | 2.50 µl |
| H$_2$O | 3.97 µl |

3.04 µl of an enzyme reagent was prepared by mixing the following components:

| | |
|---|---|
| 10 U/µl AMV reverse transcriptase (Promega) | 0.14 µl |
| 8 U/µl Bst DNA polymerase (New England Biolaboratory) | 2.27 µl |
| RNase inhibitor (Promega) | 0.63 µl |

6.00 µl of a primer reagent was prepared by mixing the following components:

| | |
|---|---|
| 80 pmol/µl forward primer | 1.00 µl |
| | SEQ ID NO: 1 |
| (5'-GGAGTTCTCAATGGTGGCACCAACTACTACACGACCATCCA-3':) | |
| 80 pmol/µl reverse inner primer | 1.00 µl |
| | SEQ ID NO: 2 |
| (5'-GTCCTGCAGATCGACAACGCCTCCGTCTCAAACTTGGTTCG-3':) | |
| 5 pmol/µl forward outer primer | 1.00 µl |
| | SEQ ID NO: 3 |
| (5'-TGGTACCAGAAGCAGGGG-3':) | |
| 5 pmol/µl reverse outer primer | 1.00 µl |
| | SEQ ID NO: 4 |
| (5'-GTTGATGTCGGCCTCCACG-3':) | |
| 60 pmol/µl forward loop primer | 1.00 µl |
| | SEQ ID NO: 5 |
| (5'-AGAATCTTGTCCCGCAGG-3':) | |
| 60 pmol/µl reverse loop primer | 1.00 µl |
| | SEQ ID NO: 6 |
| (5'-CGTCTGGCTGCAGATGA-3':) | |

(1) When agarose gel was used as the holding body

<Preparation of a Sample>

First, human lung-derived cultured cells (LC-2/ad cells obtained from Bio-resource Center in RIKEN) were recovered by trypsinization and counted with a counting chamber (manufactured by As One Corporation) under a microscope and pipetted into a 50-ml centrifuge tube such that $1.5 \times 10^6$ cells were contained per tube, to give a positive control i.

To confirm the influence of the holding body on the cells, 250 µl of 2% agarose (Agarose L03 TAKARA 5003, manufactured by Takara Bio) was pipetted into a 50-ml centrifuge tube and hardened by leaving it at 4° C. for 30 minutes, to prepare an agarose gel, and this agarose gel was washed twice with PBS and introduced into a 50-ml centrifuge tube which similar to the positive control i, contained LC-2/ad cells ($5.0 \times 10^6$ cells) to prepare comparative sample i.

250 µl of 2% agarose solution was added to a 50-ml centrifuge tube which similar to the positive control i, contained LC-2/ad cells ($5.0 \times 10^6$ cells), to suspend the cells which were then left at 4° C. for 30 minutes, thereby holding the LC-2/ad cells in agarose gel. Then, the sample was washed twice to give reference sample i-1.

<Pretreatment (Disruption)>

4 ml of the homogenizing reagent was added to each of the centrifuge tubes containing the positive control i, comparative sample i and reference sample i-1 respectively, and each sample was disrupted at 25 krpm for 90 seconds with a blender (Handy Microhomogenizer NS-350D, manufactured by Microtec Nichion) equipped with a replacement blade (built-in generator shaft NS-7, manufactured by Microtec Nichion).

<Amplification and Detection of Target Nucleic Acid>

Each of the resulting homogenates was centrifuged at 3000 rpm for 5 minutes, and 20 µl of supernatant was recovered and then diluted 10-fold with 180 µl of the homogenizing reagent.

A gene amplification detecting device (GD-100, manufactured by Sysmex Corporation) was used to amplify cDNA corresponding to CK19 mRNA in each of the measurement samples diluted with the reaction solution, the enzyme reagent and the primer reagent, and the turbidity of the solution, which was increased with the amplification, was monitored in real time, thereby detecting the concentration of the target nucleic acid (copy number per unit volume).

Figure 12:
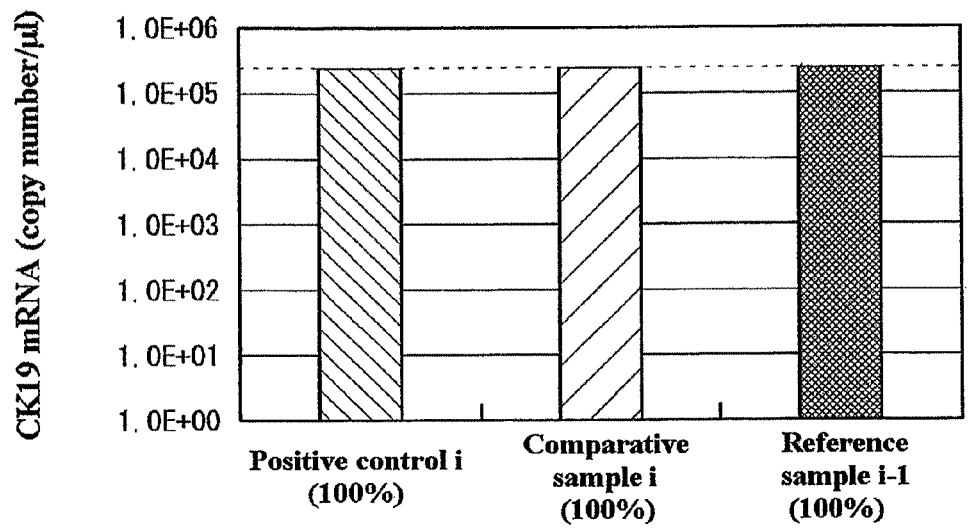
FIG. 12 is a graph showing experimental results in (1) in Example 1.

The results are shown in FIG. 12. Numbers in parentheses in FIG. 12 show the recovery of CK19 mRNA in each sample, relative to the positive control i that was assumed to be 100%.

(2) When paraffin was used as a holding body
<Preparation of a Sample>

Positive control ii was prepared in the same manner as for the positive control i except that the number of LC-2/ad cells was $1.0\times10^6$.

Paraffin (166-13285, mp. 42 to 44, manufactured by Wako Pure Chemical Industries, Ltd.) and liquid paraffin (125-04765, density (20° C.) 0.825 to 0.850 g/ml), manufactured d by Wako Pure Chemical Industries, Ltd.) were mixed at a ratio of 1:1, and 250 µl of the mixture was hardened by leaving it at 4° C. in a 50-ml centrifuge tube, and this hardened paraffin was removed and then introduced into a 50-ml centrifuge tube which similar to the positive control ii, contained LC-2/ad cells ($1.0\times10^6$ cells) to prepare comparative sample ii.

250 µl of a mixture of paraffin (mp. 42 to 44) and liquid paraffin in a ratio of 1:1 was added to a 50-ml centrifuge tube which similar to the positive control ii, contained LC-2/ad cells ($1.0\times10^6$ cells) to suspend the cells and then hardened by leaving it at 4° C., thereby holding the LC-2/ad cells in the paraffin. Then, the sample was washed twice with PBS to give reference sample ii-1.

<Pretreatment (Disruption), Amplification and Detection of Target Nucleic Acid>

The positive control ii, comparative sample ii and reference sample ii-1 were subjected to the same operation as in (1) to detect the concentration of the target nucleic acid (copy number per unit volume).

Figure 13:
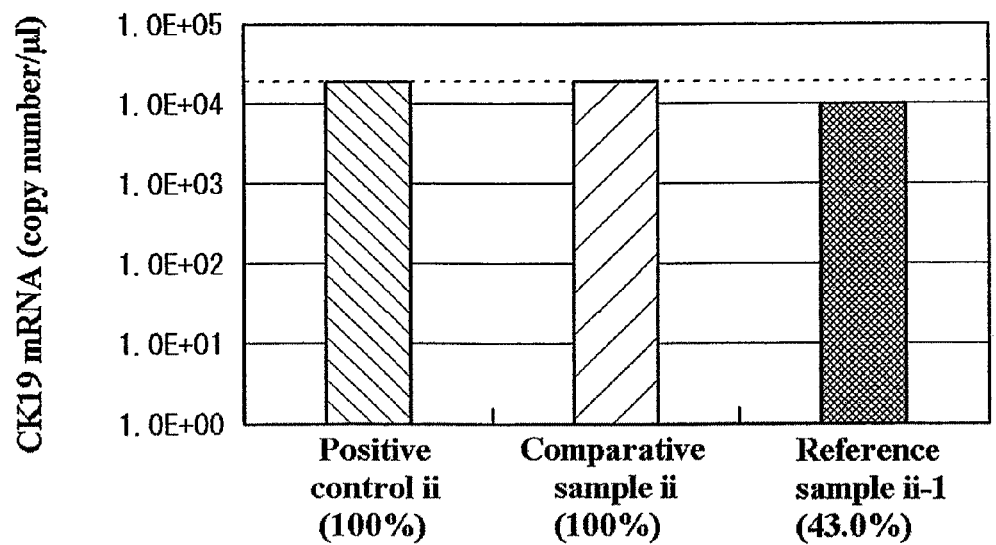
FIG. 13 is a graph showing experimental results in (2) in Example 1.

The results are shown in FIG. 13. Numbers in parentheses in FIG. 13 show the recovery of CK19 mRNA in each sample, relative to the positive control ii that was assumed to be 100%.

From FIGS. 12 and 13, it was confirmed that amplification inhibition hardly occurred in the reference sample i-1 and reference sample ii-1 wherein the cells were held with agarose gel and paraffin as the holding body.

Example 2

In a reference sample i-2 wherein cells were held with agarose gel and a reference sample ii-2 wherein cells were held with paraffin, the state of the cells was observed under an inverted microscope.

Figure 14:
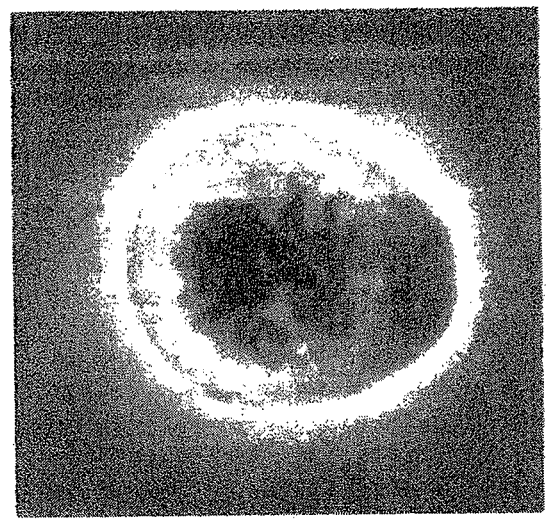
FIG. 14 is a microscope image showing the form of a cell in reference sample i-2 in Example 2.

In the reference sample i-2, LC-2/ad cells in the form of a suspension in an agarose solution was flowed and gelled on a plate for microscopic examination and then observed under an inverted microscope and photographed. FIG. 14 shows the microscope image. As can be seen from FIG. 14, the form of the cells was maintained when the cells were held with agarose gel.

Figure 15:
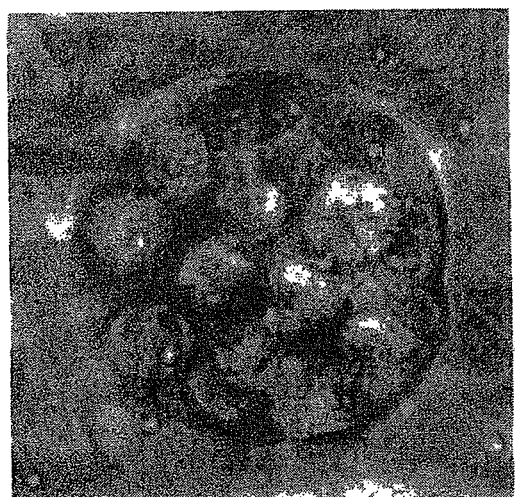
FIG. 15 is a microscope image showing the form of a cell in reference sample ii-2 in Example 2.

In the reference sample ii-2, LC-2/ad cells in the form of a suspension in liquid paraffin was flowed and gelled on a plate for microscopic examination and then observed under an inverted microscope and photographed. FIG. 15 shows the microscope image. From FIG. 15, it can be seen that when the cells were held with liquid paraffin, the cells were protected with vacuoles present around them.

Example 3

A reference sample i-3 wherein cells were held with agarose gel and a reference sample ii-3 wherein cells were held with paraffin were compared by measuring the behavior of disruption of animal-derived cell mass. As the animal-derived cell mass, 400 mg porcine lymph node was used. For the behavior of disruption, the dependence of disruption on rotation rate was examined by changing the rotation rate of a blender for a fixed rotation time, and the dependence of disruption on rotation time was examined by changing the rotation time of a blender at a fixed rotation rate.

(1) Examination of the Influence of the Rotation Rate of a Blender on Disruption First, 4 ml of the homogenizing reagent was added to the porcine lymph node which was then disrupted with the blender at 0, 5, 10, 15, 20 or 25 krpm for 90 seconds, and the resulting homogenate was centrifuged for 1 minute at 10000 G, and its intermediate layer was recovered, then diluted 100-fold with the homogenizing reagent and measured for its absorbance at 280 nm, thereby calculating the concentration of the protein corresponding to 400 mg of the lymph node. The results are shown in FIG. 16 (*a*).

The reference sample i-3 was prepared in the same manner as for the reference sample i-1 except that the number of LC-2/ad cells was $4.0\times10^5$. The sample reference i-3 was disrupted with the blender at 0, 5, 10, 15, 20 or 25 krpm for 90 seconds, and the resulting homogenate was centrifuged for 1 minute at 10000 G, and 20 µl of its intermediate layer was recovered and then diluted 10-fold with the homogenizing reagent, and then the concentration of the target nucleic acid was detected in the same manner as in <Amplification and detection of target nucleic acid> in (1) in Example 1. The results are shown in FIG. 16 (*a*).

The reference sample ii-3 was prepared in the same manner as for the reference sample ii-1. The sample reference ii-3 was disrupted with the blender at 0, 5, 10 or 25 krpm for 90 seconds, and the resulting homogenate was treated in the same manner as for the reference sample i-3 and the concentration of the target nucleic acid was detected. The results are shown in FIG. 16 (*c*).

Figure 16A:
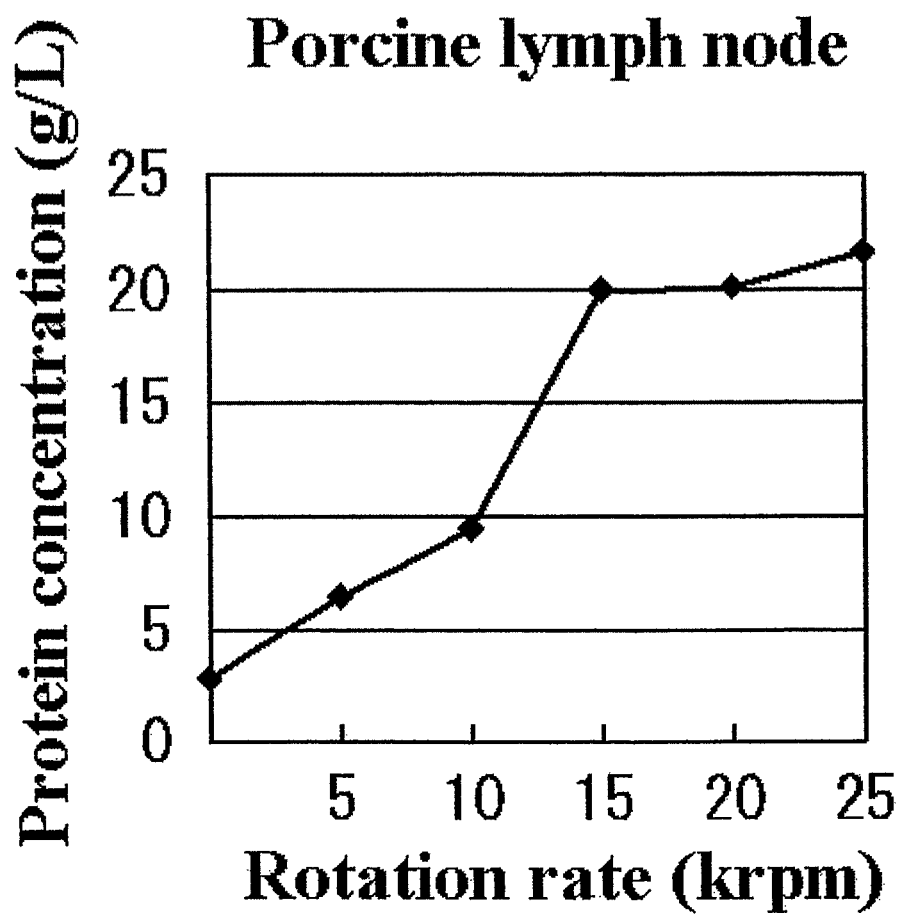
FIG. 16(a) is a graph showing experimental results of a porcine lymph node in (1) in Example 3.
Figure 16C:
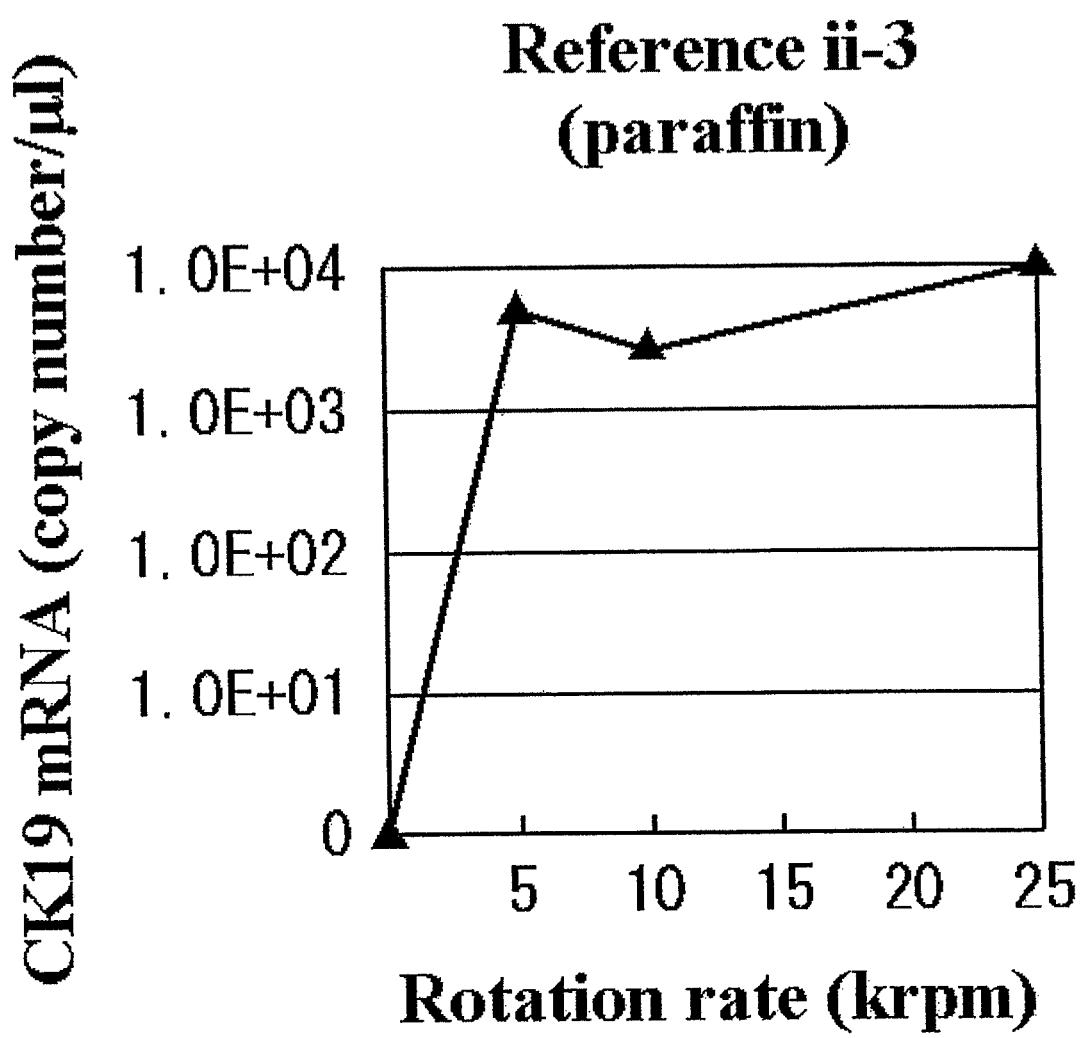
FIG. 16(c) is a graph showing experimental results of reference sample ii-3 in (1) in Example 3.

As can be seen from FIG. 16, the concentration of the protein from the porcine lymph node was increased depending on the rotation rate, while in the reference sample i-3 wherein the holding body was agarose gel and in the reference sample ii-3 wherein the holding body was paraffin, the copy number of CK19 mRNA had peaked in the stage of a rotation rate of 5 krpm.

(2) Examination of the Influence of the Disruption Time of a Blender on Disruption In the same manner as in (1), 4 ml of the homogenizing reagent was added to 400 mg of the porcine lymph node which was then disrupted with the blender at a rotation rate of 25 krpm for 0, 10, 30, 60 or 90 seconds, and subjected thereafter to the same procedure as in (1) to calculate the concentration of the protein corresponding to 400 mg of the lymph node. The results are shown in FIG. 17 (*a*).

The sample reference i-3 was disrupted with the blender at a rotation rate of 25 krpm for 0, 10, 30, 60 or 90 seconds, and subjected thereafter to the same procedure as in (1) to detect the concentration of the target nucleic acid.

The results are shown in FIG. 17 (*b*).

The sample reference ii-3 was disrupted with the blender at a rotation rate of 25 krpm for 0, 10, 30, 40, 60 or 90 seconds, and subjected thereafter to the same procedure as in (1) to detect the concentration of the target nucleic acid. The results are shown in FIG. 17 (*c*).

As can be seen from FIG. 17, the concentration of the protein from the porcine lymph node was increased depending on the disruption time, while in the reference sample i-3 wherein the holding body was agarose gel and in the reference sample ii-3 wherein the holding body was paraffin, the copy number of CK19 mRNA had peaked in the stage of a disruption time of 10 seconds. As can be seen from FIGS. 16 and 17, the cells held with the holding body are poor in strength and easily disrupted with the blender.

Example 4

Accordingly, a pseudo-tissue 1 having cells 2, a holding body 3 that holds the cells 2, a protecting body 4 that covers a part of the surface of the holding body 3 and protects the holding body 3, and an outer membrane 4 that covers the protecting body 4 was prepared. LC-2/ad cells were used as the cells 2, paraffin was used as the holding body 3, paraffin having a melting point higher than that of paraffin used as the holding body 3 was used as the protecting body 4, and a capsule consisting of gelatin was used as the outer membrane 5, and the pseudo-tissue 1 was prepared in the following manner.

Figure 7:
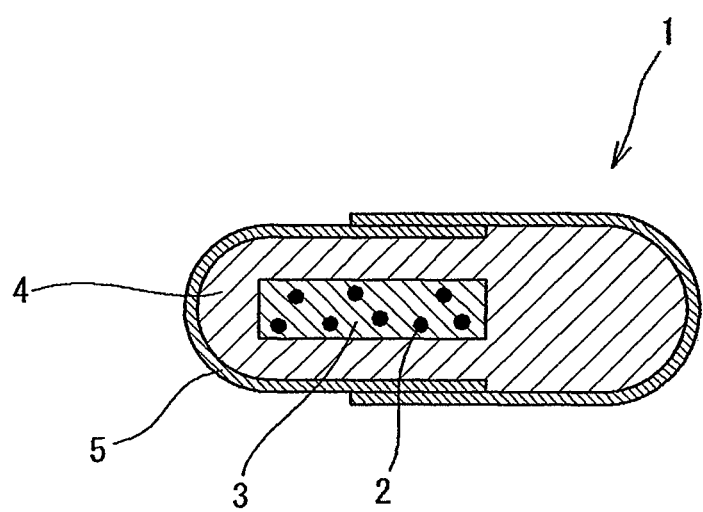
FIG. 7 is a schematic diagram showing the pseudo-tissue for accuracy control according to the present invention.
Figure 18:
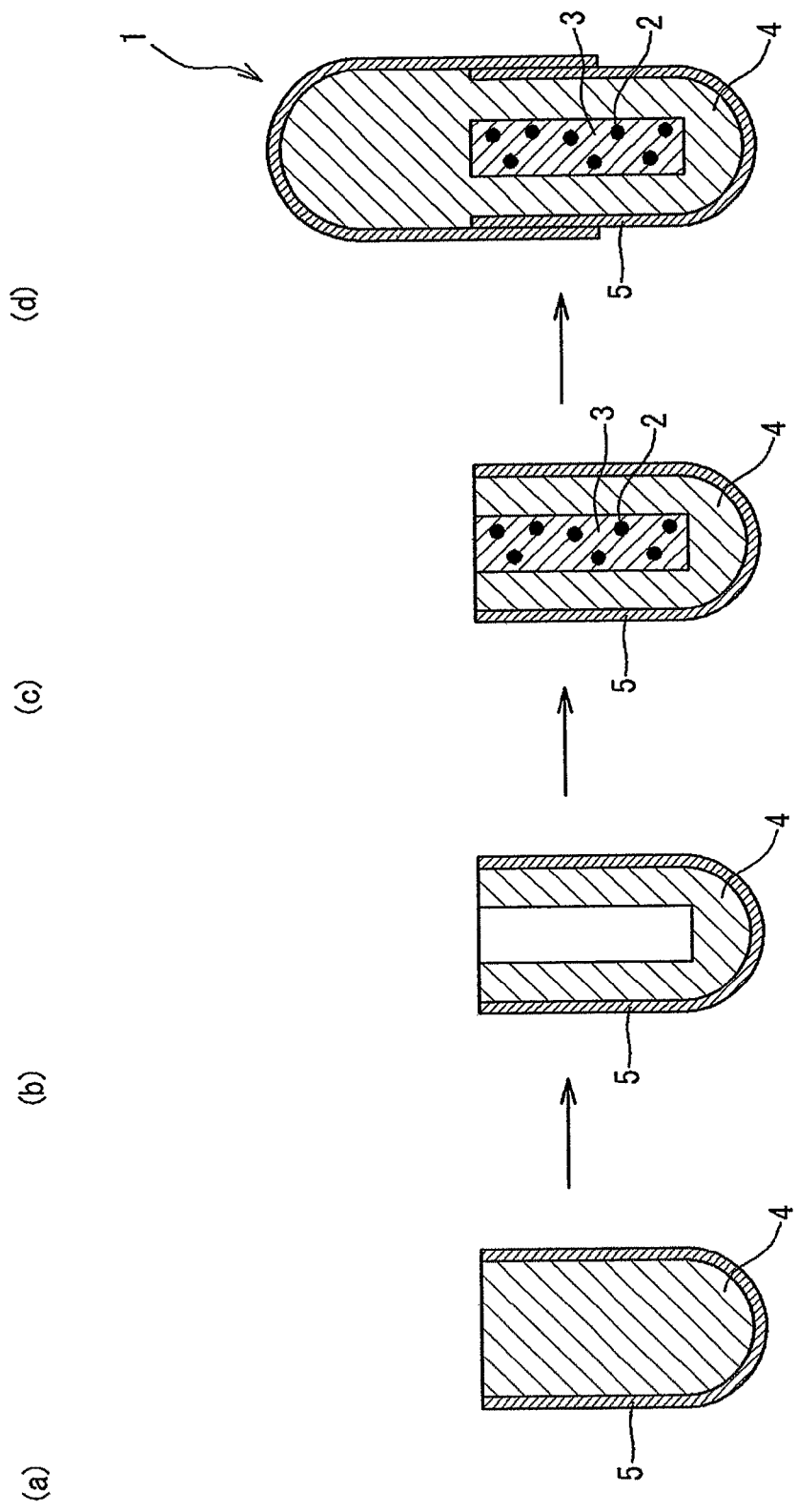
FIG. 18 is a schematic illustrative diagram showing a method for manufacturing the pseudo-tissue for accuracy control in FIG. 7.

FIG. 18 is a schematic illustrative diagram showing a method for manufacturing the pseudo-tissue 1 in FIG. 7.

300 µl of a mixture of paraffin (169-13275, mp. 44 to 46, manufactured by Wako Pure Chemical Industries, Ltd.) and paraffin (162-13385, mp. 48 to 50, manufactured by Wako Pure Chemical Industries, Ltd.) in a ratio of 1:1 was introduced into the body of a gelatin capsule (No. 00, Japanese Pharmacopoeia capsule, manufactured by Matsuya Co., Ltd.) and hardened at room temperature (see (a) in FIG. 18). Then, the hardened paraffin was provided with an opening therein with a cylinder of about 3 mm in diameter (see (b) in FIG. 13). $1.8 \times 10^6$ LC-2/ad cells suspended in 100 µl of liquid paraffin was injected into this opening, and then 300 µl of paraffin (mp. 42 to 44) was added thereto and hardened (see (c) in FIG. 18).

150 µl of a mixture of paraffin (mp. 44 to 46) and paraffin (mp. 48 to 50) in a ratio of 1:1 was also poured into a cap of the gelatin capsule and hardened, and the body was capped with this cap to prepare the pseudo-tissue 1 (see (d) in FIG. 18).

The pseudo-tissue 1 was left at −20° C., removed, introduced into a 50-ml centrifuge tube, and swollen with 4 ml homogenizing reagent for 3 minutes. Then, the pseudo-tissue 1 was disrupted with the blender at 0, 5, 10, 15, 20 or 25 krpm for 90 seconds, and subjected thereafter to the same procedure as in (1) to calculate the concentration of the target nucleic acid. The results are shown in Table 1 and FIG. 19.

TABLE 1

| Rotation rate | CK19mRNA (copy number/µl) |
|---|---|
| 0 | ND |
| 5 | 1.10E+00 |
| 10 | 2.70E+02 |
| 15 | 6.00E+03 |
| 20 | 1.10E+04 |
| 25 | 1.10E+04 |

The pseudo-tissue 1 was prepared in the same manner as described above except that the number of LC-2/ad cells suspended in 100 µl of liquid paraffin was $0.9 \times 10^6$. Then, the pseudo-tissue 1 was disrupted with the blender at a rotation rate of 25 krpm for 0, 10, 30, 40, 60 or 90 seconds, and subjected thereafter to the same procedure as in (1) to detect the concentration of the target nucleic acid. The results are shown in Table 2 and FIG. 20.

"ND" in Tables 1 and 2 indicates the case where when the copy number is a predetermined value, for example 250 or less, or in measurement data shown in FIG. 10, turbidity does not reach a threshold value even after passage of the predetermined time.

TABLE 2

| Disruption time (seconds) | CK19mRNA (copy number/µl) |
|---|---|
| 0 | ND |
| 10 | ND |
| 30 | ND |
| 40 | 1.40E+02 |
| 60 | 3.40E+02 |
| 90 | 3.40E+02 |

Figure 17A:
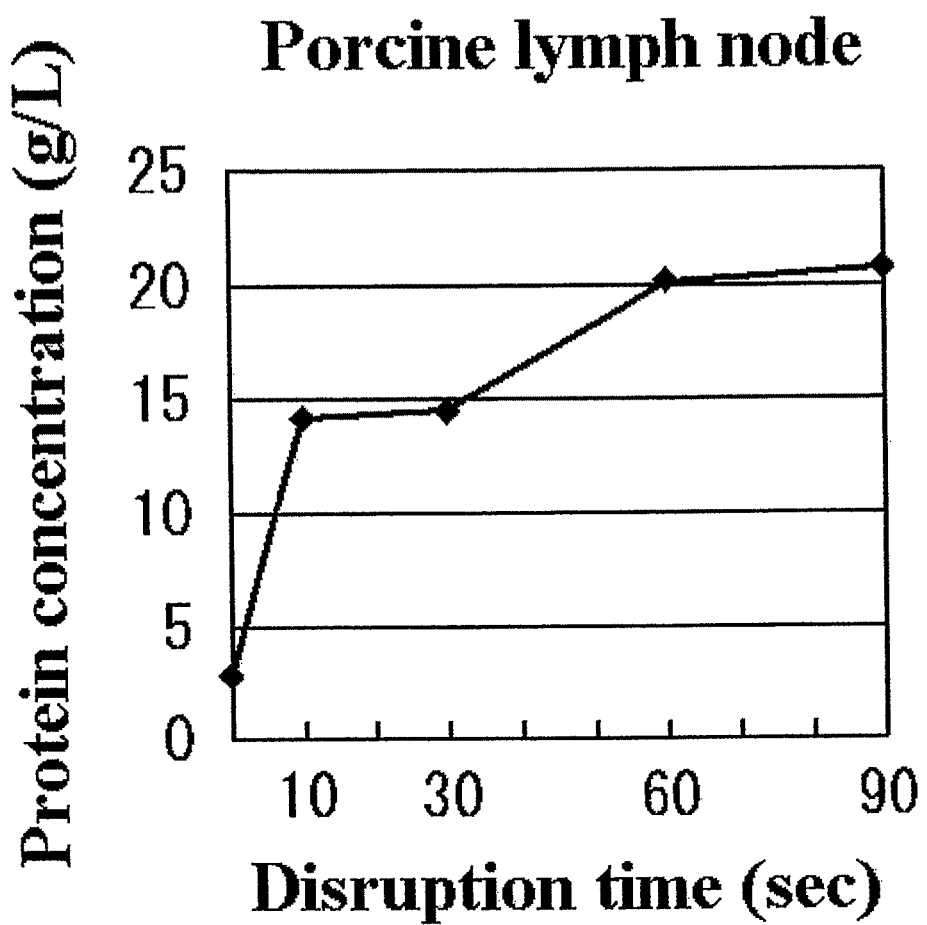
FIG. 17(a) is a graph showing experimental results of a porcine lymph node in (2) in Example 3.
Figure 19:
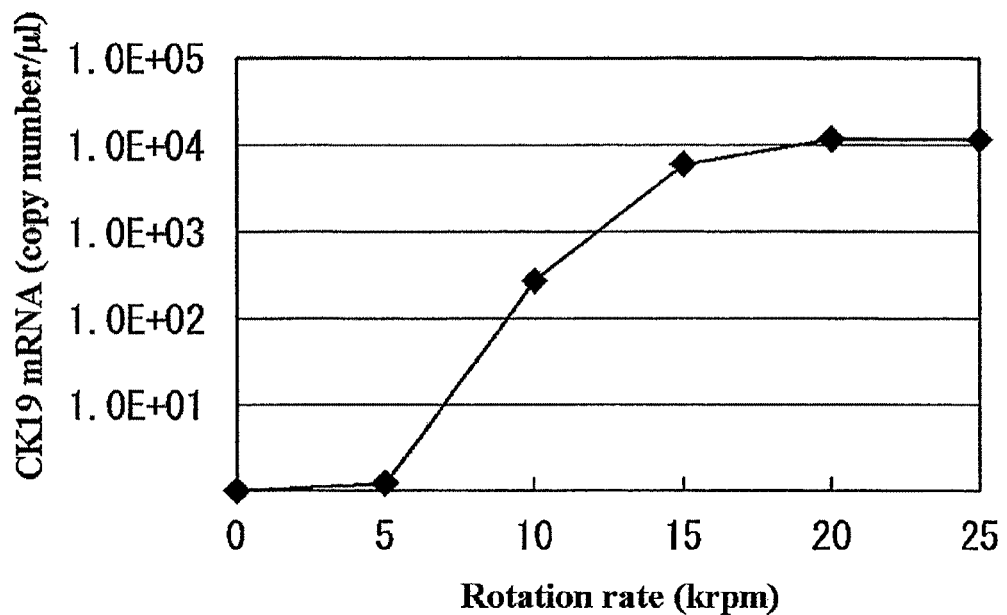
FIG. 19 is a graph showing the relationship between the number of revolutions of a blender and the copy number of CK19 mRNA in Example 4.
Figure 20:
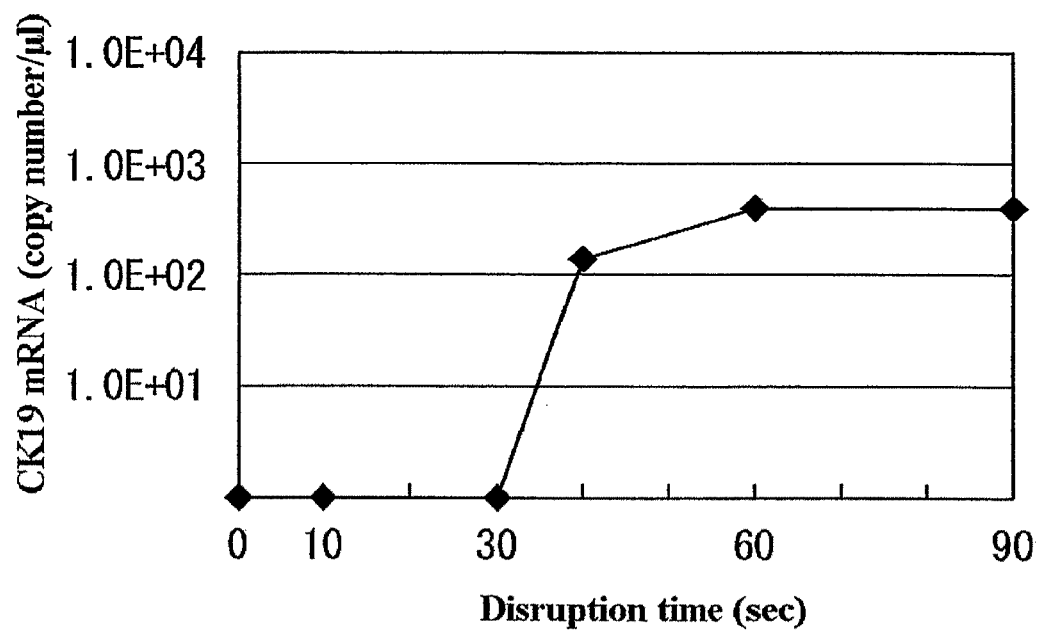
FIG. 20 is a graph showing the relationship between the disruption time of a blender and the copy number of CK19 mRNA in Example 4.

As can be seen from FIGS. 19 and 20, the pseudo-tissue 1 showed the behavior of disruption similar to that of the porcine lymph node (see FIG. 16(a) and FIG. 17(a)).

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A pseudo-tissue for accuracy control, comprising:
   cancer cells;
   a holding body for holding the cancer cells;
   a protecting body for covering the whole surface of the holding body so as to protect the holding body; and
   an outer membrane capsule for covering the whole surface of the protecting body,
   wherein both the holding body and the protecting body comprise paraffin, and the paraffin of the protecting body has a melting point higher than the paraffin of the holding body.

2. The pseudo-tissue for accuracy control according to claim 1, wherein the holding body further holds a liquid.

3. The pseudo-tissue for accuracy control according to claim 2, wherein the holding body holds the cells and the liquid, and the liquid is present as vacuoles around the cells in the holding body.

4. The pseudo-tissue for accuracy control according to claim 3, wherein the liquid comprises a cell storage solution or a buffer for washing cells.

5. The pseudo-tissue for accuracy control according to claim 1, wherein the pseudo-tissue for accuracy control is used in accuracy control in homogenization of a biological tissue, and the holding body and the protecting body are disrupted when the pseudo-tissue is homogenized.

* * * * *

SEQUENCE LISTING

<160> NUMBER OF SEQ ID NOS: 6

<210> SEQ ID NO 1
<211> LENGTH: 41
<212> TYPE: DNA
<213> ORGANISM: artificial
<220> FEATURE:
<223> OTHER INFORMATION: primer

<400> SEQUENCE: 1
ggagttctca atggtggcac caactactac acgaccatcc a        41

<210> SEQ ID NO 2
<211> LENGTH: 41
<212> TYPE: DNA
<213> ORGANISM: artificial
<220> FEATURE:
<223> OTHER INFORMATION: primer

<400> SEQUENCE: 2

```
gtcctgcaga tcgacaacgc ctccgtctca aacttggttc g                    41

<210> SEQ ID NO 3
<211> LENGTH: 18
<212> TYPE: DNA
<213> ORGANISM: artificial
<220> FEATURE:
<223> OTHER INFORMATION: primer

<400> SEQUENCE: 3
tggtaccaga agcagggg                                              18

<210> SEQ ID NO 4
<211> LENGTH: 19
<212> TYPE: DNA
<213> ORGANISM: artificial
<220> FEATURE:
<223> OTHER INFORMATION: primer

<400> SEQUENCE: 4
gttgatgtcg gcctccacg                                             19

<210> SEQ ID NO 5
<211> LENGTH: 18
<212> TYPE: DNA
<213> ORGANISM: artificial
<220> FEATURE:
<223> OTHER INFORMATION: primer

<400> SEQUENCE: 5
agaatcttgt cccgcagg                                              18

<210> SEQ ID NO 6
<211> LENGTH: 17
<212> TYPE: DNA
<213> ORGANISM: artificial
<220> FEATURE:
<223> OTHER INFORMATION: primer

<400> SEQUENCE: 6
cgtctggctg cagatga                                               17
```